United States Patent
Iwazaki et al.

(10) Patent No.: US 9,194,315 B2
(45) Date of Patent: Nov. 24, 2015

(54) AIR-FUEL RATIO IMBALANCE AMONG CYLINDERS DETERMINING APPARATUS FOR AN INTERNAL COMBUSTION ENGINE

(75) Inventors: Yasushi Iwazaki, Ebina (JP); Hiroshi Miyamoto, Susono (JP); Hiroshi Sawada, Gotemba (JP); Keiichiro Aoki, Sunto-gun (JP)

(73) Assignee: Toyota Jidosha Kabushiki Kaisha, Toyota-shi (JP)

(*) Notice: Subject to any disclaimer, the term of this patent is extended or adjusted under 35 U.S.C. 154(b) by 400 days.

(21) Appl. No.: 13/144,194

(22) PCT Filed: Nov. 26, 2009

(86) PCT No.: PCT/JP2009/070274
§ 371 (c)(1),
(2), (4) Date: Jul. 12, 2011

(87) PCT Pub. No.: WO2011/064899
PCT Pub. Date: Jun. 3, 2011

(65) Prior Publication Data
US 2011/0271665 A1 Nov. 10, 2011

(51) Int. Cl.
*F01N 3/10* (2006.01)
*G01N 7/00* (2006.01)
*F02D 41/00* (2006.01)
(Continued)

(52) U.S. Cl.
CPC ........ *F02D 41/0085* (2013.01); *F02D 41/1475* (2013.01); *G01N 27/419* (2013.01); *F02D 41/1441* (2013.01); *F02D 41/1454* (2013.01)

(58) Field of Classification Search
CPC ............ F02D 41/0085; F02D 41/1475; F02D 41/1441

USPC ..................... 60/285; 73/23.32; 204/424–429
See application file for complete search history.

(56) References Cited

U.S. PATENT DOCUMENTS

| 7,152,594 B2 | 12/2006 | Anilovich et al. |
| 7,356,985 B2* | 4/2008 | Hirata et al. ................. 60/274 |
| 8,407,983 B2* | 4/2013 | Mukai ........................ 60/277 |

(Continued)

FOREIGN PATENT DOCUMENTS

| JP | 11072473 A | 3/1999 |
| JP | 2000065782 A | 3/2000 |

(Continued)

*Primary Examiner* — Audrey K Bradley
*Assistant Examiner* — Jason Sheppard
(74) *Attorney, Agent, or Firm* — Dinsmore & Shohl LLP

(57) ABSTRACT

An air-fuel ratio imbalance among cylinders determining apparatus (a determining apparatus) according to an aspect of the present invention, obtains a parameter X for imbalance determination which becomes larger as a variation of an air-fuel ratio of an exhaust gas passing through a position at which the air-fuel ratio sensor is disposed becomes larger, based on an output value Vabyfs of an air-fuel ratio sensor 67. At the same time, the determining apparatus changes a target air-fuel ratio which is a target value of an air-fuel ratio of a mixture supplied to an engine to "an air-fuel ratio (a target rich air-fuel ratio AFrich or a target lean air-fuel ratio AFlean) other than a stoichiometric air-fuel ratio" from the stoichiometric air-fuel ratio. Accordingly, the determining apparatus can obtain the parameter X for imbalance determination in a state in which a responsivity of the air-fuel ratio sensor 67 is not low. As a result, it can make a determination on the air-fuel ratio imbalance among cylinders with high accuracy.

3 Claims, 15 Drawing Sheets

(51) Int. Cl.
  *G01N 27/419* (2006.01)
  *F02D 41/14* (2006.01)

(56) References Cited

U.S. PATENT DOCUMENTS

2007/0089482 A1* 4/2007 Uchikawa et al. ........... 73/23.32
2007/0144905 A1* 6/2007 Tsuji et al. .................... 204/424
2007/0240695 A1* 10/2007 Mitsuda et al. ............... 123/673

FOREIGN PATENT DOCUMENTS

| JP | 2003-328848 A | 11/2003 |
| JP | 2004069547 A | 3/2004 |
| JP | 2009-013967 A | 1/2009 |
| JP | 2009-074388 A | 4/2009 |
| JP | 2009-209747 A | 9/2009 |
| JP | 2009264184 A | 11/2009 |
| JP | 2009264287 A | 11/2009 |
| WO | WO-2009013600 A2 | 1/2009 |

* cited by examiner

AIR-FUEL RATIO IMBALANCE AMONG CYLINDERS DETERMINING APPARATUS FOR AN INTERNAL COMBUSTION ENGINE

TECHNICAL FIELD

The present invention relates to "an air-fuel ratio imbalance among cylinders determining apparatus for an internal combustion engine", which is applied to a multi-cylinder internal combustion engine, and which can determine (or monitor, detect) whether or not an imbalance of an air-fuel ratio of an air-fuel mixture supplied to each of cylinders (i.e., an air-fuel ratio imbalance among the cylinders, variation in air-fuel ratios among the cylinders, or air-fuel ratio non-uniformity among the cylinders) becomes excessively large.

BACKGROUND ART

Conventionally, an air-fuel ratio control apparatus has been widely known, which comprises a three-way catalytic converter (53) disposed in an exhaust passage of an internal combustion engine, and an upstream-side air-fuel ratio sensor (67) and a downstream-side air-fuel ratio sensor (68) disposed upstream and downstream of the three-way catalytic converter (53), respectively, as shown in FIG. 1.

The air-fuel ratio control apparatus calculates an air-fuel ratio feedback amount based on an output of the upstream-side air-fuel ratio sensor and an output of the downstream-side air-fuel ratio sensor, and feedback controls an air-fuel ratio of a mixture supplied to the engine (an air-fuel ratio of the engine) with the air-fuel ratio feedback amount, so that the air-fuel ratio of the engine coincides with the stoichiometric air-fuel ratio. Further, an air-fuel ratio control apparatus has also been widely known, which calculates "an air-fuel ratio feedback amount to make the air-fuel ratio of the engine coincide with the stoichiometric air-fuel ratio" based only on the output of the upstream-side air-fuel ratio sensor, and feedback controls the air-fuel ratio of the engine with the feedback amount. The air-fuel ratio feedback amount used in those air-fuel ratio control apparatuses is a control amount commonly used for all of the cylinders.

Meanwhile, an electronic control fuel injection type internal combustion engine, typically, comprises at least one fuel injector (39) in each of the cylinders or in each of the intake ports, each communicating with each of the cylinders. Accordingly, when a characteristic of an injector for a specific cylinder becomes "a characteristic that the injector injects fuel by an amount which is larger (more excessive) than an instructed fuel injection amount", only an air-fuel ratio of a mixture supplied to the specific cylinder (air-fuel-ratio-of-the-specific-cylinder) changes toward extremely richer side. That is, an imbalance among air-fuel ratios of the cylinders (a variation in air-fuel ratios among the cylinders, air-fuel ratio non-uniformity among the cylinders) becomes large. In other words, there arises an imbalance among "the individual-cylinder-air-fuel-ratios", each of which is an air-fuel ratio of a mixture supplied to each of the cylinders.

In this case, an average of the air-fuel ratios of the mixtures supplied to the entire engine becomes an air-fuel ratio richer (smaller) than a stoichiometric air-fuel ratio. Accordingly, the feedback amount common to all of the cylinders causes the air-fuel ratio of the specific cylinder to change to a leaner (larger) air-fuel ratio so that the air-fuel ratio of the specific cylinder is made closer to the stoichiometric air-fuel ratio, and at the same time, the feedback amount causes the air-fuel ratios of the other cylinders to change to a leaner (larger) air-fuel ratios so that the air-fuel ratios of the other cylinders are made deviate more from the stoichiometric air-fuel ratio. As a result, the average of the air-fuel ratios of the mixtures supplied to the entire engine is made roughly equal to the stoichiometric air-fuel ratio.

However, the air-fuel ratio of the specific cylinder is still richer (smaller) than the stoichiometric air-fuel ratio, and the air-fuel ratios of the other cylinders are still leaner (larger) than the stoichiometric air-fuel ratio, and therefore, a combustion condition of the mixture in each of the cylinders is different from a perfect combustion. As a result, an amount of emissions (an amount of an unburnt substances and/or an amount of nitrogen oxides) discharged from each of the cylinders increases. Accordingly, although the average of the air-fuel ratios of the mixtures supplied to the engine coincides with the stoichiometric air-fuel ratio, the three-way catalytic converter can not purify the increased emission, and thus, there is a possibility that the emission becomes worse.

It is therefore important to detect whether or not the air-fuel ratio non-uniformity among cylinders becomes excessively large (an air-fuel ratio imbalance among cylinders is occurring), because an appropriate measure can be taken in order not to worsen the emissions. It should be noted that the air-fuel ratio imbalance among cylinders occurs when a characteristic of an injector of a specific cylinder becomes "a characteristic that the injector injects fuel by an amount which is excessively smaller than the instructed fuel injection amount".

One of such conventional apparatuses that determine whether or not the air-fuel ratio imbalance among cylinders is occurring obtains a trajectory length of an output value (output signal) of an air-fuel ratio sensor (the above mentioned upstream-side air-fuel ratio sensor 67) disposed at an exhaust-gas-aggregated-portion to which exhaust gases from a plurality of cylinders aggregate, compares the trajectory length with "a reference value varying in accordance with an engine rotational speed", and that determines whether or not the air-fuel ratio imbalance among cylinders is occurring based on the comparison result (refer to, for example, U.S. Pat. No. 7,152,594).

It should be noted that, in the present specification, "an occurrence of the air-fuel ratio imbalance among cylinders" means an occurrence of a state in which a difference between individual cylinder air-fuel ratios (individual cylinder air-fuel-ratio difference) is greater than or equal to a tolerable value, and in other words, it means an occurrence of an excessive air-fuel ratio imbalance among cylinders which causes the unburnt substances and/or the nitrogen oxides to exceed predetermined tolerable values. "Determining (judging) whether or not the air-fuel ratio imbalance among cylinders is occurring" can be simply referred to as "a determination of an air-fuel ratio imbalance among cylinders, or an imbalance determination". Furthermore, a cylinder to which an air-fuel mixture is supplied, whose air-fuel ratio is different (or apart) from an air-fuel ratio (e.g., the stoichiometric air-fuel ratio) of an air-fuel mixture supplied to each of the other cylinders, is also referred to as "an imbalance cylinder". The air-fuel mixture supplied to the imbalance cylinder is also referred to as "an imbalance cylinder air-fuel ratio". Each of the other cylinders (each cylinder other than the imbalance cylinder) is also referred to as "a normal cylinder" or "an un-imbalance cylinder". The air-fuel mixture supplied to the normal cylinder is also referred to as "a normal cylinder air-fuel ratio" or "an un-imbalance cylinder air-fuel ratio".

In addition, a value which increases as an absolute value of the individual cylinder air-fuel-ratio difference (an absolute value of a difference between the imbalance cylinder air-fuel ratio and the normal cylinder air-fuel ratio) increases, just like the trajectory length of the output value of the air-fuel ratio sensor, may be referred to as an air-fuel-ratio-variation-indicative-value. That is, the air-fuel-ratio-variation-indicative-value is "a value which is obtained based on the output value of the air-fuel ratio sensor" in such a manner that its absolute value becomes greater as a variation of the air-fuel ratio of the exhaust gas arriving at the above mentioned air-fuel ratio sensor becomes greater. Further, a value, which becomes greater as an absolute value of the air-fuel-ratio-variation-indicative-value becomes greater, and which is obtained based on the air-fuel-ratio-variation-indicative-value, can be referred to as "a parameter for imbalance determination (judgment)". The parameter for imbalance determination is compared with a threshold value for imbalance determination in order to perform the imbalance determination.

SUMMARY OF THE INVENTION

In the meantime, the well-known air-fuel ratio sensor comprises an air-fuel ratio detection portion including at least "a solid electrolyte layer (671), an exhaust-gas-side electrode layer (672), an atmosphere-side electrode layer (673), and a diffusion resistance layer (674)", as shown in (A) of FIG. 2. The exhaust-gas-side electrode layer (672) is formed on one surface of the solid electrolyte layer (671). The exhaust-gas-side electrode layer (672) is covered by the diffusion resistance layer (674). An exhaust gas in the exhaust gas passage reaches an outer surface of the diffusion resistance layer (674), and then passes through the diffusion resistance layer (674) to reach the exhaust-gas-side electrode layer (672). The atmosphere-side electrode layer (673) is formed on the other surface of the solid electrolyte layer (671). The atmosphere-side electrode layer (673) is exposed to an atmosphere chamber (678) into which an atmosphere is introduced.

As shown in (B) and (C) of FIG. 2, an electric voltage (Vp) is applied between the exhaust-gas-side electrode layer (672) and the atmosphere-side electrode layer (673), the electric voltage (Vp) being for generating "a limiting-current varying in accordance with an air-fuel ratio of the exhaust gas". The electric voltage is typically applied in such a manner that an electric potential of the atmosphere-side electrode layer (673) is higher than an electric potential of the exhaust-gas-side electrode layer (672).

As shown in (B) of FIG. 2, when the exhaust gas reaching the exhaust-gas-side electrode layer (672) after passing through the diffusion resistance layer (674) contains excessive oxygen (i.e., an air-fuel ratio of the exhaust gas reaching the exhaust-gas-side electrode layer is leaner (larger) than the stoichiometric air-fuel ratio), the oxygen is led, in a form of an oxygen ion, to the atmosphere-side electrode layer (673) from the exhaust-gas-side electrode layer (672), owing to the above mentioned electric voltage and an oxygen pump characteristics of the solid electrolyte layer (671).

To the contrary, as shown in (C) of FIG. 2, when the exhaust gas reaching the exhaust-gas-side electrode layer (672) after passing through the diffusion resistance layer (674) contains excessive unburnt substances (i.e., the air-fuel ratio of the exhaust gas reaching the exhaust-gas-side electrode layer is smaller (richer) than the stoichiometric air-fuel ratio), the oxygen in the atmosphere chamber (678) is led, in a form of an oxygen ion, to the exhaust-gas-side electrode layer (672) from the atmosphere-side electrode layer (673), owing to an oxygen cell characteristics of the solid electrolyte layer (671), and the oxygen reacts with the unburnt substances on the exhaust-gas-side electrode layer (672).

An amount of such oxygen ion movement is limited to a value depending on "an air-fuel ratio of the exhaust gas reaching the outer surface of the diffusion resistance layer (674)", owing to an existence of the diffusion resistance layer (674). In other words, an electric current generated by the oxygen ion movement shows a value (i.e., a limiting current Ip) varying in accordance with the air-fuel ratio (A/F) of the exhaust gas (refer to FIG. 3).

The air-fuel ratio sensor outputs an output value Vabyfs varying depending on (in accordance with) "the air-fuel ratio of the exhaust gas passing through a position at which the air-fuel ratio sensor is disposed" based on the limiting current (the current flowing thorough the solid electrolyte layer caused by applying the voltage between the exhaust-gas-side electrode layer and the atmosphere-side electrode layer). The output value Vabyfs is typically converted into a detected air-fuel ratio abyfs, based on a predetermined "relationship, shown in FIG. 4, between the output value Vabyfs and the air-fuel ratio". As understood from FIG. 4, the output value Vabyfs is substantially proportional to the detected air-fuel ratio abyfs.

Meanwhile, the air-fuel-ratio-variation-indicative-value which is "a basic data for the parameter for imbalance determination" is not limited to the trajectory length of "the output value of the air-fuel ratio sensor or the detected air-fuel ratio abyfs", but may be a value indicative of a variation (or a fluctuation) state of the air-fuel ratio of the exhaust gas passing through the position at which the air-fuel ratio sensor is disposed (e.g., a variation amount (amplitude, width) of the air-fuel ratio in a predetermined period). This will be further described below.

The exhaust gas from each of the cylinders reaches the air-fuel ratio sensor in order of ignition (and thus, in order of discharging the exhaust gas). When the air-fuel ratio imbalance among cylinders is not occurring, each of the air-fuel ratios of the exhaust gas discharged from each of the cylinders is substantially equal to each other. Accordingly, as shown by a dotted line C1 in (B) of FIG. 5, when the air-fuel ratio imbalance among cylinders is not occurring, the wave shape of the output value Vabyfs of the air-fuel ratio sensor (represented as a wave shape of the detected air-fuel ratio abyfs in (B) of FIG. 5) is substantially flat.

To the contrary, when "the air-fuel ratio imbalance among cylinders (i.e., a specific cylinder rich-side deviation imbalance state) in which only an air-fuel ratio of the specific cylinder (e.g., the first cylinder) deviates toward richer side than the stoichiometric air-fuel ratio" is occurring, there is a great difference between the air-fuel ratio of the specific cylinder and the air-fuel ratio of any one of cylinders (the other cylinder) other than the specific cylinder.

Accordingly, for example, as shown by a solid line C2 in (B) of FIG. 5, when the specific cylinder rich-side deviation imbalance state is occurring, the wave shape of the output value Vabyfs of the air-fuel ratio sensor (represented as the wave shape of the detected air-fuel ratio abyfs in (B) of FIG. 5) varies greatly every 720° crank angle in the case of the 4-cylinder and 4-cycle engine (i.e., every predetermined crank angle which is necessary for each of the cylinders to complete one combustion stroke, each of the cylinders discharging an exhaust gas which reaches the single air-fuel ratio sensor). It should be noted that, "a time period for which the predetermined crank angle passes, the predetermined crank angle being necessary for each of the cylinders to complete one combustion stroke, each of the cylinders discharging an exhaust gas which reaches the single air-fuel ratio sensor" is referred to as "a unit combustion cycle period", in the present specification.

Further, an amplitude of the output value Vabyfs of the air-fuel ratio sensor and an amplitude of the detected air-fuel ratio become larger so that those values fluctuate (vary) more greatly, as the air-fuel ratio of the imbalance cylinder deviate more greatly from the air-fuel ratio of the normal cylinder. For example, assuming that a detected air-fuel ratio abyfs varies as shown by a solid line C2 in FIG. 5 (B) when the largeness (absolute value) of the difference between the air-fuel ratio of the imbalance cylinder and the air-fuel ratio of the un-imbalance cylinder is a first value, a detected air-fuel ratio abyfs varies as shown by an alternate long and short dash line C2a in FIG. 5 (B) when the largeness (absolute value) of the difference between the air-fuel ratio of the imbalance cylinder and the air-fuel ratio of the un-imbalance cylinder is "a second value larger than the first value".

Accordingly, a variation amount (change amount) of "the output value Vabyfs of the air-fuel ratio sensor or the detected air-fuel ratio abyfs" per unit time (i.e., a first order differential value of "the output value Vabyfs of the air-fuel ratio sensor or the detected air-fuel ratio abyfs" with respect to time, or an angles $\alpha1$, $\alpha2$ in (B) of FIG. 5) becomes smaller, when the individual cylinder air-fuel-ratio difference is small as shown by a dotted line C3 in (C) of FIG. 5, and becomes large when the individual cylinder air-fuel-ratio difference is large as shown by a solid line C4 in (C) of FIG. 5. That is, absolute values of the differential value d(Vabyfs)/dt and the differential value d(abyfs)/dt become greater, as a degree of air-fuel ratio imbalance becomes greater (i.e., as the individual cylinder air-fuel-ratio difference becomes larger).

Accordingly, for example, a maximum value or an average value of absolute values of "the differential value d(Vabyfs)/dt and the differential value d(abyfs)/dt", the values being obtained multiple times during the unit combustion cycle period, can be adopted as the air-fuel-ratio-variation-indicative-value. Further, the air-fuel-ratio-variation-indicative-value itself or a mean value of the air-fuel-ratio-variation-indicative-values for a plurality of unit combustion cycle periods can also be adopted as the parameter for imbalance determination.

Furthermore, as shown in (D) of FIG. 5, a variation amount (change amount) of the variation amount (the change amount) of "the output value Vabyfs of the air-fuel ratio sensor or the detected air-fuel ratio abyfs" per unit time (i.e., a second order differential value $d^2$(Vabyfs)/$dt^2$ or a second order differential value $d^2$(abyfs)/$dt^2$) varies little when the individual cylinder air-fuel-ratio difference is small as shown by a dotted line C5, and varies greatly when the individual cylinder air-fuel-ratio difference is large as shown by a solid line C6.

Accordingly, for example, "a maximum value or an average value" of absolute values of "the second order differential value $d^2$(Vabyfs)/$dt^2$ or the second order differential value $d^2$(abyfs)/$dt^2$", the values being obtained multiple times during the unit combustion cycle period, can be adopted as the air-fuel-ratio-variation-indicative-value. Further, the air-fuel-ratio-variation-indicative-value itself or a mean value of the air-fuel-ratio-variation-indicative-values for a plurality of unit combustion cycle periods can also be adopted as the parameter for imbalance determination.

Further, the air-fuel ratio imbalance among cylinders determining apparatus determines if the air-fuel ratio imbalance (state) is occurring by determining whether or not the thus obtained parameter for imbalance determination is larger than a predetermined threshold value (a threshold value for imbalance determination).

However, the present inventors have found that, when the air-fuel ratio of the exhaust gas fluctuates in an air-fuel region which is very close to the stoichiometric air-fuel ratio, the state occurs in which "the output value Vabyfs of the air-fuel ratio sensor does not vary with respect to (or in response to) the fluctuation in the air-fuel ratio of the exhaust gas with having high responsivity (the state in which the responsivity of the air-fuel ratio sensor becomes poor or low)", and therefore, the parameter for imbalance determination obtained based on the air-fuel-ratio-variation-indicative-value does not indicate "a degree of the air-fuel ratio imbalance (state) among cylinders" with an adequate precision, and accordingly, a case arises in which air-fuel ratio imbalance determination can not be performed with high accuracy. It should be noted that the above mentioned "air-fuel region which is very close to the stoichiometric air-fuel ratio" is an air-fuel region having a certain range which includes the stoichiometric air-fuel ratio, and can be referred to as "the stoichiometric air-fuel ratio region". Further, "the degree of the air-fuel ratio imbalance (state) among cylinders" means the individual cylinder air-fuel-ratio difference, that is, the difference between the imbalance cylinder air-fuel ratio and the normal cylinder air-fuel ratio.

FIG. 6 is a graph to explain the above described phenomenon. The axis of ordinate of FIG. 6 corresponds to the parameter for imbalance determination obtained based on the differential value d(abyfs)/dt. The axis of abscissas of FIG. 6 corresponds to an average value of "the air-fuel ratios of the exhaust gas passing through the position at which the air-fuel sensor is disposed" for a period in which the parameter for imbalance determination (or more accurately, the air-fuel-ratio-variation-indicative-value which is the basic data for the parameter for imbalance determination) is obtained. The average value of the air-fuel ratios of the exhaust gas can be referred to as "a parameter obtaining period average air-fuel ratio".

A curve line C1 of FIG. 6 shows the parameter for imbalance determination, when the difference between individual cylinder air-fuel-ratios is extremely small, and therefore, when it is not necessary to determine that the air-fuel ratio imbalance (state) among cylinders is occurring.

A curve line C2 of FIG. 6 shows the parameter for imbalance determination, when the difference between individual cylinder air-fuel-ratios is larger than one in the case shown by the curve line C1, however, when it is still not necessary to determine that the air-fuel ratio imbalance (state) among cylinders is occurring.

A curve line C3 of FIG. 6 shows the parameter for imbalance determination, when the difference between individual cylinder air-fuel-ratios is larger than one in the case shown by the curve line C2, and therefore, when it is necessary to determine that the air-fuel ratio imbalance (state) among cylinders is occurring.

A curve line C4 of FIG. 6 shows the parameter for imbalance determination, when the difference between individual cylinder air-fuel-ratios is extremely large (i.e., larger than one in the case shown by the curve line C3), and therefore, when it is necessary to determine that the air-fuel ratio imbalance (state) among cylinders is occurring.

As is clear from FIG. 6, the parameter for imbalance determination which is obtained when the parameter obtaining period average air-fuel ratio is within "the stoichiometric air-fuel ratio region" which is, for example, roughly between 14.2 and 15.0 is smaller than any one of the parameter for imbalance determination which is obtained when the parameter obtaining period average air-fuel ratio is within "a rich region (for example, a region in which the air-fuel ratio is smaller or equal to 14.2) and the parameter for imbalance determination which is obtained when the parameter obtaining period average air-fuel ratio is within "a lean region (for example, a region in which the air-fuel ratio is larger than or equal to 15.0)"

Accordingly, if it is determined that the air-fuel ratio imbalance (state) among cylinders is occurring when the parameter for imbalance determination is larger than the threshold value for imbalance determination (refer to a line L1 of FIG. 6), there is a possibility that it is determined that the air-fuel ratio imbalance (state) among cylinders is not occurring when it should be determined that the air-fuel ratio imbalance (state) among cylinders is occurring (refer to the value shown by the line C3, in a region in which the air-fuel ratio is close to the stoichiometric air-fuel ratio), or that it is determined that the air-fuel ratio imbalance (state) among cylinders is occurring when it should be determined that the air-fuel ratio imbalance (state) among cylinders is not occurring (refer to the value shown by the line C2 in the rich region or in the lean region).

It should be noted that it is inferred that the reason why the responsivity of the air-fuel ratio sensor becomes lower when the air-fuel ratio of the exhaust gas varies within the stoichiometric air-fuel ratio region (i.e., when the parameter obtaining period average air-fuel ratio is within the stoichiometric air-fuel ratio region) is that, when the air-fuel ratio of the exhaust gas changes from "an air-fuel ratio richer (i.e., smaller) than the stoichiometric air-fuel ratio" to "an air-fuel ratio leaner (i.e., larger) than the stoichiometric air-fuel ratio", or vice versa, a direction of the reaction at the exhaust-gas-side electrode layer must change to a reverse direction, and thus, it requires a considerable time for a direction of the Oxygen ions passing through the solid electrolyte layer to be reversed.

Accordingly, one of objects of the present invention is to provide an air-fuel ratio imbalance among cylinders determining apparatus (hereinafter, simply referred to as a present invention apparatus), which is capable of performing the determination of an air-fuel ratio imbalance among cylinders with high precision.

The present invention apparatus sets a target air-fuel ratio to (at) "a non-stoichiometric air-fuel ratio which is other than the stoichiometric air-fuel ratio" in a period for which it obtains the parameter for imbalance determination. This allows the apparatus to obtain the parameter for imbalance determination in a state where (or when) the responsivity of the air-fuel sensor is not low.

More specifically, one of the aspects of the present invention apparatus is applied to a multi-cylinder internal combustion engine having a plurality of cylinders, and comprises an air-fuel ratio sensor, a plurality of fuel injectors, instructed fuel injection amount control means, and imbalance determining means.

The air-fuel ratio sensor is disposed at an exhaust-gas-aggregated-portion of an exhaust gas passage of the engine, to (into) which exhaust gases discharged from at least two cylinders of the plurality of cylinders aggregate, or is disposed at a position downstream of the exhaust-gas-aggregated-portion in the exhaust gas passage.

Further, the air-fuel ratio sensor includes an air-fuel ratio detection section having a solid electrolyte layer, an exhaust-gas-side electrode layer formed on one of surfaces of the solid electrolyte layer, a diffusion resistance layer which covers the exhaust-gas-side electrode layer and at which the exhaust gas arrives, an atmosphere-side electrode layer formed on the other of surfaces of the solid electrolyte layer so as to be exposed to an air in an atmosphere chamber. The air-fuel ratio sensor outputs an output value varying depending on an air-fuel ratio of the exhaust gas passing through the position at which the air-fuel ratio sensor is disposed, based on "a limiting-current flowing through the solid electrolyte layer, the limiting-current being generated by applying a predetermined electrical voltage between the exhaust-gas-side electrode layer and the atmosphere-side electrode layer".

Each of the plurality of the fuel injectors is provided (disposed) corresponding to or for each of at least two or more cylinders, and injects a fuel contained in a mixture supplied to each of combustion chambers of the two or more cylinders. That is, one or more of the fuel injector(s) is/are provided per one cylinder. Each of the fuel injectors injects the fuel for each of the cylinders to which the fuel injector corresponds.

The instructed fuel injection amount control means controls an instructed fuel injection amount in such a manner that an air-fuel ratio of the mixture supplied to the combustion chambers of the two or more of the cylinders coincides with (becomes equal to) a target air-fuel ratio. The instructed fuel injection amount control means may include an air-fuel ratio feedback control means for calculating an air-fuel ratio feedback amount based on the air-fuel ratio represented by the output value of the air-fuel ratio sensor and the target air-fuel ratio in such a manner that these two values coincide with each other, and for determining (adjusting controlling) the instructed fuel injection amount based on the air-fuel ratio feedback amount. Alternatively, the instructed fuel injection amount control means may be a feedforward control means for adopting (determining), as the instructed fuel injection amount, a value obtained by dividing a cylinder intake air amount (an air amount introduced into one cylinder in one intake cycle) determined based on, for example, an intake air flow rate and an engine rotational speed, by the target air-fuel ratio, without including the air-fuel ratio feedback control means.

The imbalance determining means, (1) obtains a parameter for imbalance determination which becomes larger (or increases) as a variation (or a fluctuation) of the air-fuel ratio of the exhaust gas passing through the position at which the air-fuel ratio sensor is disposed becomes larger (changes more greatly), (2) determines that an air-fuel ratio imbalance state among cylinders is occurring when the obtained parameter for imbalance determination is larger than a predetermined threshold value for imbalance determination, and (3) determines that the air-fuel ratio imbalance state among cylinders is not occurring when the obtained parameter for imbalance determination is smaller than the predetermined threshold value for imbalance determination.

The parameter for imbalance determination may be, but not limited to, for example, "a maximum value or a mean value" of absolute values of the above described "differential value d(Vabyfs)/dt or differential value d(abyfs)/dt" for a predetermined period (for example, the above mentioned unit combustion cycle period), "a maximum value or a mean value" of absolute values of the "second order differential value $d^2$(Vabyfs)/$dt^2$ or second order differential value $d^2$(abyfs)/$dt^2$" for a predetermined period (for example, the above mentioned unit combustion cycle period), a trajectory length of "the output value Vabyfs or the detected air-fuel ratio abyfs" for a predetermined period (for example, the above mentioned unit combustion cycle period), or the like, or a value based on these values.

Furthermore, the imbalance determining means is configured in such a manner that, it sets the target air-fuel ratio to (at) "a non-stoichiometric air-fuel ratio which is an air-fuel ratio other than the stoichiometric air-fuel ratio" and obtains the parameter for imbalance determination in a period in which a predetermined condition for obtaining a parameter for imbalance determination is satisfied, and it sets the target air-fuel ratio to (at) the stoichiometric air-fuel ratio in a period in which the predetermined condition for obtaining a parameter for imbalance determination is not satisfied.

It should be noted that it is not always necessary for the target air-fuel ratio to be set at the stoichiometric air-fuel ratio in the period in which the predetermined condition for obtaining a parameter for imbalance determination is not satisfied. In other words, even in the period in which the predetermined condition for obtaining a parameter for imbalance determination is not satisfied, the target air-fuel ratio may be set to (at) an air-fuel ratio other than the stoichiometric air-fuel ratio in a particular case, such as a period immediately after an engine start or a period immediately after an end of a fuel cut control.

According to the above described configuration, the parameter for imbalance determination is obtained based on the output value of the air-fuel ratio sensor, when the air-fuel ratio of the exhaust gas of the engine varies in proximity to the non-stoichiometric air-fuel ratio while the target air-fuel ratio is set at the non-stoichiometric air-fuel ratio, that is, when the output value of the air-fuel ratio sensor can vary depending on (or follow) the variation (fluctuation) of the air-fuel ratio of the exhaust gas without a long delay.

Therefore, according to the present invention apparatus, the parameter for imbalance determination can be a value which represents the degree of the air-fuel ratio imbalance state among cylinders (i.e., the difference between individual cylinder air-fuel-ratios) with great accuracy, and thus, it is possible to determine whether or not the air-fuel ratio imbalance state among cylinders is occur-ring with great certainty.

It should be noted that the condition for obtaining a parameter for imbalance determination may include one or more of conditions selecting from, for example, a condition that an imbalance determination has not been performed yet after the current engine start, a condition that the intake air flow rate is larger than or equal to a constant value (or within a predetermined range), a condition that the engine rotational speed is within a predetermined range, a condition that a temperature of an engine coolant is higher than or equal to a engine coolant temperature threshold, a condition that a predetermined time has passed since a variation amount in a throttle valve opening angle or an operation amount of an accelerator pedal becomes lower than or equal to a predetermined value, and so on. Note that the condition for obtaining a parameter for imbalance determination is not limited to the above conditions.

In addition, the non-stoichiometric air-fuel ratio to which the target air-fuel ratio is set is an air-fuel ratio (an air-fuel ratio different from the stoichiometric air-fuel ratio by a predetermined air-fuel ratio) such that the output value of the air-fuel ratio sensor can adequately follow a variation or a fluctuation of the air-fuel ratio of the exhaust gas, when the air-fuel ratio of the exhaust gas is equal to or in the vicinity of the non-stoichiometric air-fuel ratio.

In the mean time, if the difference between individual cylinder air-fuel-ratios is extremely large, a variation (a fluctuation) of the air-fuel ratio of the exhaust gas is extremely large. Accordingly, the parameter for imbalance determination obtained under such condition becomes extremely large (refer to a curve line C4 in FIG. 6), even when the responsivity of the air-fuel ratio sensor is relatively low or poor while the air-fuel ratio of the exhaust gas varies in the vicinity of the stoichiometric air-fuel ratio. Therefore, if the parameter for imbalance determination is obtained when the target air-fuel ratio is set at the stoichiometric air-fuel ratio, and the thus obtained parameter for imbalance determination is larger than "a predetermined threshold (which is also referred to as a high side threshold value, see a line L2 in FIG. 6)", it is possible to determine clearly that "the air-fuel ratio imbalance state among cylinders is occurring".

To the contrary, if the difference between individual cylinder air-fuel-ratios is extremely small, a variation (a fluctuation) of the air-fuel ratio of the exhaust gas is extremely small. Therefore, even when the parameter for imbalance determination is obtained in a case in which the responsivity of the air-fuel ratio sensor is relatively low or poor while the air-fuel ratio of the exhaust gas varies in the vicinity of the stoichiometric air-fuel ratio, it is possible to determine clearly that "the air-fuel ratio imbalance state among cylinders is not occurring" if the parameter for imbalance determination is extremely small. In other words, if the parameter for imbalance determination which is obtained when the air-fuel ratio of the exhaust gas varies in the vicinity of the stoichiometric air-fuel ratio is smaller than "a threshold value (referred to as a low side threshold value, see a line L3 in FIG. 6) which is smaller than the high side threshold value by a predetermined value", it is possible to determine clearly that "the air-fuel ratio imbalance state among cylinders is not occurring" (refer to a curve line C1 in FIG. 6).

Accordingly, the imbalance determining means may be configured in such a manner that the imbalance determining means (4) maintains the target air-fuel ratio at the stoichiometric air-fuel ratio and obtains the parameter for imbalance determination as a tentative parameter based on the output value of the air-fuel ratio sensor before it sets the target air-fuel ratio to (at) the non-stoichiometric air-fuel ratio in the period in which the predetermined condition for obtaining a parameter for imbalance determination is satisfied, and (5) determines that "the air-fuel ratio imbalance state among cylinders is occurring", when the obtained tentative parameter is larger than "the predetermined high side threshold value", and (6) determines that the air-fuel ratio imbalance state among cylinders is not occurring, when the obtained tentative parameter is smaller than "the low side threshold value which is smaller than the high side threshold value by the predetermined value (amount)".

In this case, it is preferable that the high side threshold value be a value larger than or equal to the threshold value for imbalance determination, and the low side threshold value be a value smaller than the threshold value for imbalance determination.

Meanwhile, if the parameter for imbalance determination which is obtained in a case in which the responsivity of the air-fuel ratio sensor is relatively low or poor because the air-fuel ratio of the exhaust gas varies in the vicinity of the stoichiometric air-fuel ratio is between the high side threshold value and the low side threshold value, it is not possible to determine clearly whether or not the air-fuel ratio imbalance state among cylinders is occurring.

Accordingly, the imbalance determining means may be configured in such a manner that the imbalance determining means (7) defers (or suspends) a determination as to whether or not the air-fuel ratio imbalance state among cylinders is occurring when the obtained tentative parameter is smaller than the high side threshold value and larger than the low side threshold value, (8) sets the target air-fuel ratio at the non-stoichiometric air-fuel ratio and obtains the parameter for imbalance determination based on the output value of the air-fuel ratio sensor as a final parameter, in a period in which the predetermined condition for obtaining a parameter for imbalance determination is satisfied in a case in which the determination as to whether or not the air-fuel ratio imbalance state among cylinders is occurring is deferred (or suspended), and (9) determines that the air-fuel ratio imbalance state among cylinders is occurring when the obtained final parameter is larger than the threshold value for imbalance determination, and determines that the air-fuel ratio imbalance state among cylinders is not occurring when the obtained final parameter is smaller than the threshold value for imbalance determination.

According to the configuration described above, it is possible to obtain the parameter for imbalance determination (the final parameter) in a state in which the responsivity of the air-fuel sensor is high (quick). Therefore, it is possible to make a determination on the air-fuel ratio imbalance among cylinders with high accuracy by using the final parameter, even when it is not possible to determine clearly whether or not the air-fuel ratio imbalance state among cylinders is occurring by using the tentative parameter.

Moreover, according to the configuration described above, it is not necessary to set the target air-fuel ratio at the non-stoichiometric air-fuel ratio, if it is possible to determine clearly "whether or not the air-fuel ratio imbalance state among cylinders is occurring" based on the parameter for imbalance determination (the tentative parameter) which is obtained in a state in which the responsivity of the air-fuel sensor is relatively low (poor). As a result, it is possible to decrease frequency of having worse emission.

In the present invention apparatus, the air-fuel ratio detection section of the air-fuel ratio sensor may include a catalytic section which facilitates an oxidation-reduction reaction and has an oxygen storage function; and the air-fuel sensor may be configured in such a manner that the exhaust gas passing through the exhaust gas passage reaches the diffusion resistance layer via the catalytic section.

For example, an average value of the air-fuel ratio of the exhaust gas changes to a certain rich air-fuel ratio, when the rich-side deviation imbalance state is occurring. In this case, more unburnt substances including Hydrogen are formed, compared to a case in which each of air-fuel ratios of all cylinders is uniformly changed to the certain rich air-fuel ratio. Hydrogen can pass through the diffusion resistance layer of the air-fuel ratio detection section more easily than the other unburnt substances, because a particle size of hydrogen is small. As a result, the output value of the air-fuel ratio sensor changes to a value corresponding to an air-fuel ratio which is richer (smaller) than the certain rich air-fuel ratio. Accordingly, there is a possibility that the air-fuel ratio feedback control based on the output value of the air-fuel ratio sensor can not be performed properly.

On the other hand, if the catalytic section is provided to the air-fuel ratio sensor, it is possible to decrease an amount of excessive hydrogen contained in the exhaust gas reaching the exhaust-gas-side electrode layer, because the excessive hydrogen can be oxidized by the catalytic section. As a result, the output value of the air-fuel ratio sensor comes closer to a value representing (indicative of) the air-fuel ratio of the exhaust gas with high accuracy.

However, "a change in the output value of the air-fuel ratio sensor with respect to a variation in the air-fuel ratio of the exhaust gas" is delayed, due to the oxidation-reduction reaction and the oxygen storage function of the catalytic section. As a result, the responsivity of the air-fuel ratio sensor is lowered (becomes slower), compared to the air-fuel ratio sensor which does not comprise the catalytic section. The delay in the output value of the air-fuel ratio sensor due to the oxygen storage function becomes notably longer, especially when the air-fuel ratio of the exhaust gas fluctuates with crossing up and down the stoichiometric air-fuel ratio. Accordingly, the parameter for imbalance determination becomes much smaller, when the air-fuel ratio of the exhaust gas varies in the vicinity of the stoichiometric air-fuel ratio (that is, when the parameter obtaining period average air-fuel ratio is close to the stoichiometric air-fuel ratio). In view of the above, the present invention apparatus can provide a significant advantage in a case where the imbalance determination is made using the parameter for imbalance determination obtained based on such output value of the air-fuel ratio sensor comprising the above catalytic section, in the internal combustion engine having the air-fuel ratio sensor.

Furthermore, the air-fuel sensor often comprises a protective cover, which accommodates the air-fuel ratio detecting section in its inside so as to cover the air-fuel detecting section, which includes inflow holes for the exhaust gas passing through the exhaust gas passage to flow into the inside of the cover and outflow holes for the exhaust gas flowed into the inside of the cover to flow out to the exhaust gas passage.

In this case, it is preferable that the parameter for imbalance determination obtaining means be configured in such a manner that it obtains, as a basic indicative value, a differential value with respect to time of "the output value of the air-fuel ratio sensor or a detected air-fuel ratio which is an air-fuel ratio represented by the output value", and obtains the parameter for imbalance determination based on the obtained basic indicative value.

Unless the difference between individual cylinder air-fuel-ratios is equal to "0", the output value Vabyfs of the air-fuel ratio sensor periodically varies with having the unit combustion cycle period as one period. Accordingly, the trajectory length of the output value Vabyfs is strongly affected by the engine rotational speed. It is therefore necessary to accurately set the threshold value for imbalance determination in accordance with the engine rotational speed.

To the contrary, if the air-fuel ratio sensor comprises the above described protective cover, a flow rate of the exhaust gas in the protective cover does not depend on the engine rotational speed, but depends on a flow rate of the exhaust gas flowing in the exhaust gas passage (and therefore, depends on the intake air flow rate). This is because, the exhaust gas flows into the inside of the protective cover through the inflow holes by a negative pressure generated by the exhaust gas flowing in the vicinity of the outflow holes of the protective cover.

Accordingly, if the intake air flow rate is constant, "the differential value d(Vabyfs)/dt with respect to time of the output value Vabyfs of the air-fuel ratio sensor, or the differential value d(abyfs)/dt with respect to time of the detected air-fuel ratio which is the air-fuel ratio represented by the output value of the air-fuel ratio sensor" does not depend on the engine rotational speed, and can indicate with high accuracy the variation (fluctuation) of the air-fuel ratio of the exhaust gas. Accordingly, it is possible to obtain the parameter for imbalance determination as a value accurately representing the difference between individual cylinder air-fuel-ratios regardless of whether or not the engine rotational speed is high, by obtaining, as the basic indicative value, these differential values, and obtaining the parameter for imbalance determination based on the obtained basic indicative value.

Alternatively, it is preferable that the parameter for imbalance determination obtaining means be configured in such a manner that it obtains, as a basic indicative value, a second order differential value with respect to time of the output value of the air-fuel ratio sensor or a detected air-fuel ratio which is an air-fuel ratio represented by the output value of the air-fuel ratio sensor, and obtains the parameter for imbalance determination based on the obtained basic indicative value.

The second order differential value ($d^2(Vabyfs)/dt^2$, or $d^2(abyfs)/dt^2$) with respect to time of the output value of the air-fuel ratio sensor or the detected air-fuel ratio which is the air-fuel ratio represented by the output value of the air-fuel ratio sensor is hardly affected by a graduate (slow) change in an average value of the air-fuel ratio of the exhaust gas. Accordingly, it is possible to obtain the parameter for imbalance determination as "a value accurately representing the difference between individual cylinder air-fuel-ratios" even when the average value of the air-fuel ratio of the exhaust gas varies relatively gradually, by obtaining, as the basic indicative value, these second order differential values, and by obtaining the parameter for imbalance determination based on the obtained basic indicative value.

DESCRIPTION OF THE EMBODIMENT

Each of air-fuel ratio imbalance among cylinders determining apparatuses (hereinafter, simply referred to as "a determining apparatus") for an internal combustion engine according to each of the embodiments of the present invention will next be described with reference to the drawings. The determining apparatus is a portion of an air-fuel ratio control apparatus for controlling an air-fuel ratio of a mixture supplied to the internal combustion engine (the air-fuel ratio of the engine), and also, a portion of a fuel injection amount control apparatus for controlling a fuel injection amount.

First Embodiment

Structure

Figure 7:
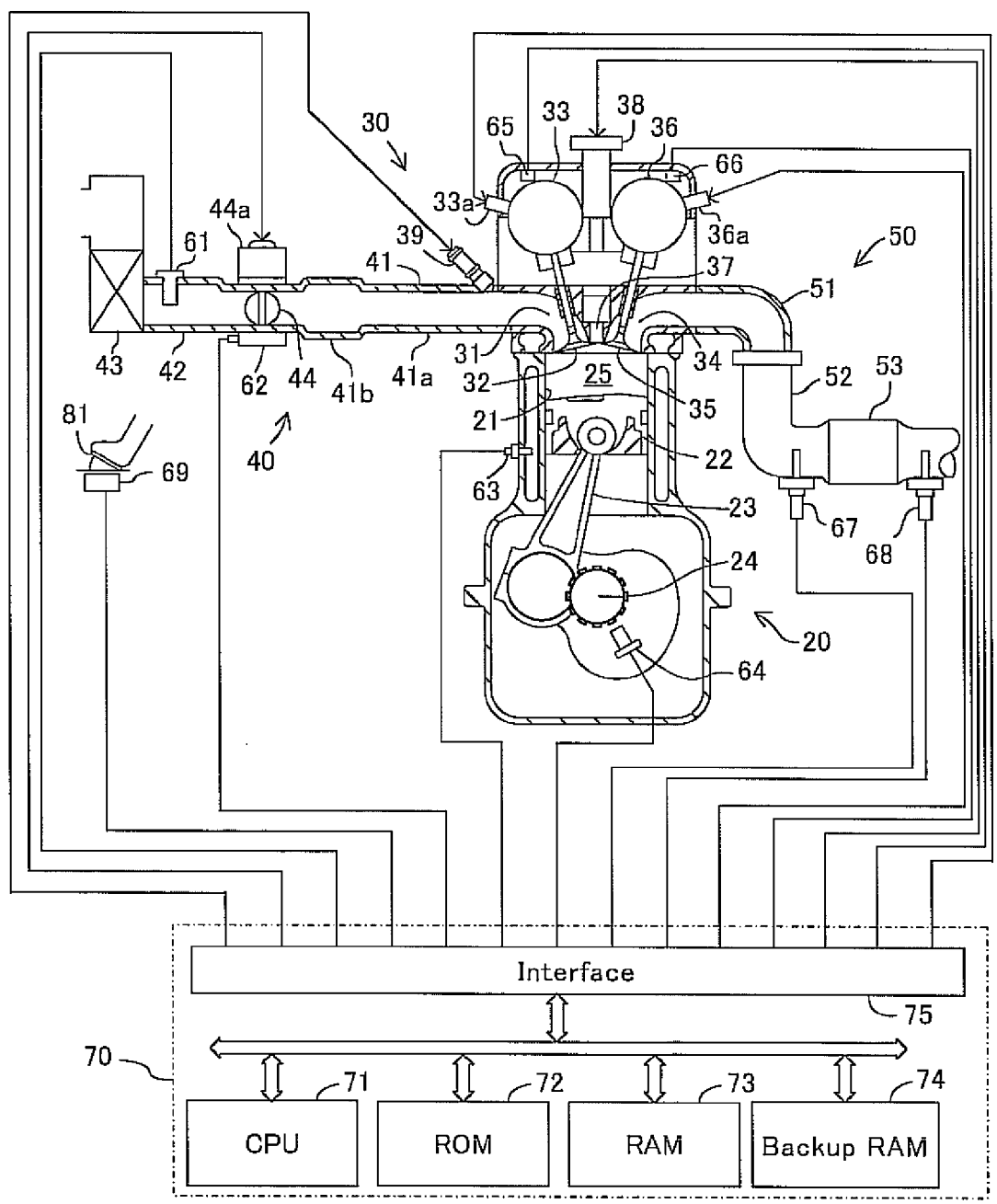
FIG. 7 is a schematic sectional view of the internal combustion engine shown in FIG. 1.

FIG. 7 schematically shows the configuration of a system configured such that a determining apparatus according to a first embodiment (hereinafter also referred to as the "first determining apparatus") is applied to a 4 cycle, spark-ignition, multi-cylinder (e.g., in line 4 cylinder) internal combustion engine 10. It should be noted that FIG. 7 shows a sectional view of a specific cylinder, however, the other cylinders have similar configurations.

This internal combustion engine 10 includes a cylinder block section 20 including a cylinder block, a cylinder block lower-case, an oil pan, etc.; a cylinder head section 30 fixed on the cylinder block section 20; an intake system 40 for supplying gasoline gas mixture to the cylinder block section 20; and an exhaust system 50 for discharging exhaust gas from the cylinder block section 20 to the exterior of the engine.

The cylinder block section 20 includes cylinders 21, pistons 22, connecting rods 23, and a crankshaft 24. Each of the pistons 22 reciprocates within the corresponding cylinder 21. The reciprocating motion of the piston 22 is transmitted to the crankshaft 24 via the respective connecting rod 23, whereby the crankshaft 24 is rotated. A wall surface of the cylinder 21 and an upper surface of the piston 22 form a combustion chamber 25 in cooperation with a lower surface of the cylinder head section 30.

The cylinder head section 30 includes intake ports 31 communicating with the combustion chambers 25; intake valves 32 for opening and closing the intake ports 31; a variable intake timing control unit 33 including an intake cam shaft for driving the intake valves 32 and continuously changing the phase angle of the intake cam shaft; an actuator 33a of the variable intake timing control unit 33; exhaust ports 34 communicating with the combustion chambers 25; an exhaust valves 35 for opening and closing the exhaust ports 34; a variable exhaust timing control unit 36 including an exhaust cam shaft for driving the exhaust valves 35 and continuously changing the phase angle of the exhaust cam shaft; an actuator 36a of the variable exhaust timing control unit 36; spark plugs 37; an igniters 38 each including an ignition coil for generating a high voltage to be applied to each of the spark plugs 37; and fuel injectors (fuel injection means, fuel supply means) 39.

The fuel injectors 39 are provided in such a manner that there is a single (one) fuel injector for each of the combustion chambers 25. Each of the fuel injector 39 is disposed at each of the intake ports 31. The fuel injector 39 is configured in such a manner that it is responsive to an injection instruction signal to thereby inject "a fuel of an instructed fuel injection amount contained in the injection instruction signal" into a corresponding intake port 31 when the fuel injector is normal. In this manner, each of a plurality of cylinders comprises the fuel injector 39 which supplies the fuel to each of the cylinder, independently from the other cylinders.

The intake system 40 includes an intake manifold 41; an intake pipe 42, an air filter 43, and a throttle valve 44.

Figure 1:
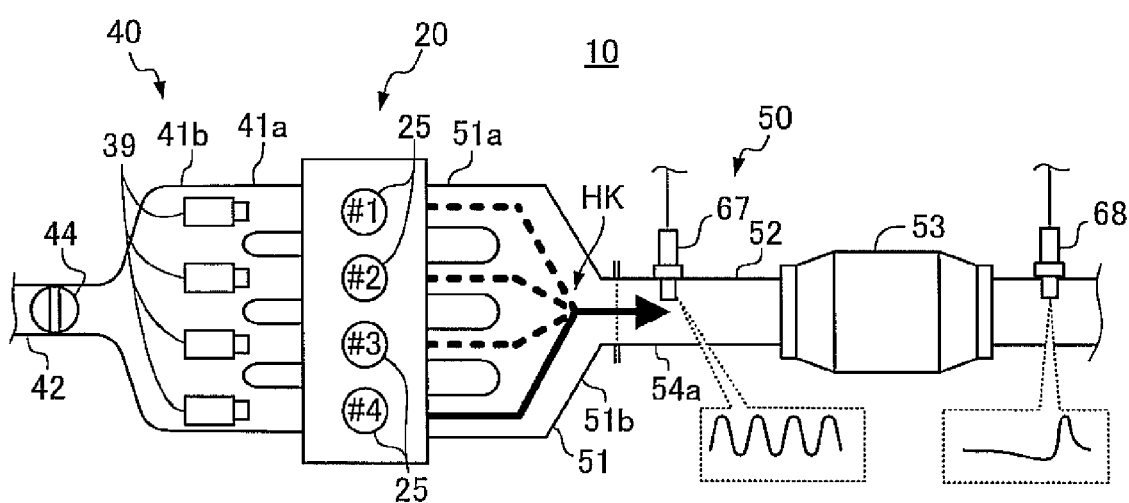
FIG. 1 is a schematic top view of an internal combustion engine to which an air-fuel ratio imbalance among cylinders determining apparatus according to each of embodiments of the present invention is applied.

As shown in FIG. 1, the intake manifold 41 includes a plurality of branch portions 41a and a surge tank 41b. One of ends of each of the plurality of branch portions 41a is connected to each of the plurality of the intake ports 31, as shown in FIG. 7. The other one of the ends of each of the plurality of branch portions 41a is connected to the surge tank 41b. One of ends of the intake pipe 42 is connected to the surge tank 41b. The air filter 43 is provided at the other one of the ends of the intake pipe 42. The throttle valve 44 is within the intake pipe 42 so as to change an opening cross sectional area of the intake passage. The throttle valve 44 is configures in such a manner that it is rotatably driven within the intake pipe 42 by the throttle valve actuator (a portion of throttle valve drive means) 44a comprising a DC motor.

The exhaust system 50 includes an exhaust manifold 51, an exhaust pipe 52, an upstream-side catalyst 53 disposed in the exhaust pipe 52, and a downstream-side catalyst (not shown) disposed at a position downstream of the upstream-side catalyst 53 in the exhaust pipe 52.

As shown in FIG. 1, the exhaust manifold 51 comprises a plurality of branch portions 51a, each of which ends is connected to each of the exhaust ports, and a merging portion 51b, which is located at the other ends of the branch portions 51a, and into which all of the branch portions 51a merge. The merging portion 51b is also referred to as an exhaust-gas-aggregated-portion HK (an exhaust gas merging portion HK), because exhaust gases discharged from a plurality of (two or more, four in the present example) cylinders gather in or aggregate to the portion. The exhaust pipe 52 is connected to the merging portion 51b. As shown in FIG. 7, the exhaust ports 34, the exhaust manifold 51, and the exhaust pipe 52 constitute an exhaust passage.

Each of the upstream-side catalyst 53 and the downstream-side catalyst is a three-way catalytic unit (exhaust gas purifying catalyst) which supports so called active components comprising a noble (precious) metal (catalytic substance) including Platinum, Rhodium, Palladium, and so on. Each of the catalysts has a function to oxidize unburnt substances such as HC, CO, and $H_2$ and to reduce nitrogen oxide (NOx), when an air-fuel ratio of a gas flowing into each of the catalysts is the stoichiometric air-fuel ratio. This function may be referred to as a catalytic function. Further, each of the catalysts has an oxygen storage function to store oxygen, the oxygen storage function enabling the catalysts to purify the unburnt substances and the nitrogen oxide even when the air-fuel ratio deviates from the stoichiometric air-fuel ratio. This oxygen storage function is brought by a substance for storing oxygen such as ceria ($CeO_2$) supported by each of the catalysts.

As shown in FIG. 7, this system includes a hot-wire air flowmeter 61, a throttle position sensor 62, a water temperature sensor 63, a crank position sensor 64, an intake cam position sensor 65, an exhaust cam position sensor 66, an upstream-side (upstream) air-fuel ratio sensor 67, a downstream-side (downstream) air-fuel ratio sensor 68, and an accelerator opening sensor 69.

The air flowmeter 61 outputs a signal corresponding to a mass flow rate (an intake air flow rate) Ga of an intake air flowing through the intake pipe 42. That is, the intake air flow rate Ga is indicative of an amount of air introduced into the engine 10 per unit time.

The throttle position sensor 62 detects the opening of the throttle valve (throttle valve opening angle) 44, and outputs a signal representing the throttle valve opening TA.

The water temperature sensor 63 detects a temperature of cooling water of the engine 10, and outputs a signal representing the cooling water temperature THW.

The crank position sensor 64 outputs a signal which includes a narrow pulse generated every time the crank shaft 24 rotates 10 degrees and a wide pulse generated every time crank shaft 24 rotates 360 degrees. This signal is converted into a signal representing an engine rotational speed NE by an electric controller 70, which will be described later.

The intake cam position sensor 65 outputs one pulse every time the intake cam shaft rotates from a predetermined angle by 90 degrees, further rotates by 90 degrees, and further rotates by 180 degrees. The electric controller 70 described later obtains, based on the signals from the crank position sensor 64 and the intake cam position sensor 65, an absolute crank angle (crankshaft angle) CA whose reference (origin) is a top dead center on the compression stroke of a reference cylinder (e.g., the first cylinder). The absolute crank angle CA is set to (at) "0° crank angle" at the top dead center on the compression stroke of the reference cylinder, is increased up to 720° crank angle, and then is set to (at) "0° crank angle" again.

The exhaust cam position sensor 66 outputs one pulse every time the exhaust cam shaft rotates from a predetermined angle by 90 degrees, further rotates by 90 degrees, and further rotates by 180 degrees.

As also shown in FIG. 1, the upstream-side air-fuel ratio sensor 67 (the air-fuel ratio sensor in the present invention) is disposed at a position between the merging portion 51b (the exhaust-gas-aggregated-portion HK) of the exhaust manifold 51 and the upstream-side catalyst 53 and in either one of "the exhaust manifold 51 and the exhaust pipe 52 (that is, in the exhaust passage)". The upstream-side air-fuel ratio sensor 67 is "a wide range air-fuel ratio sensor of a limiting current type having a diffusion resistance layer" described in, for example, Japanese Patent Application Laid-Open (kokai) No. Hei 11-72473, Japanese Patent Application Laid-Open No. 2000-65782, and Japanese Patent Application Laid-Open No. 2004-69547, etc.

Figure 8:
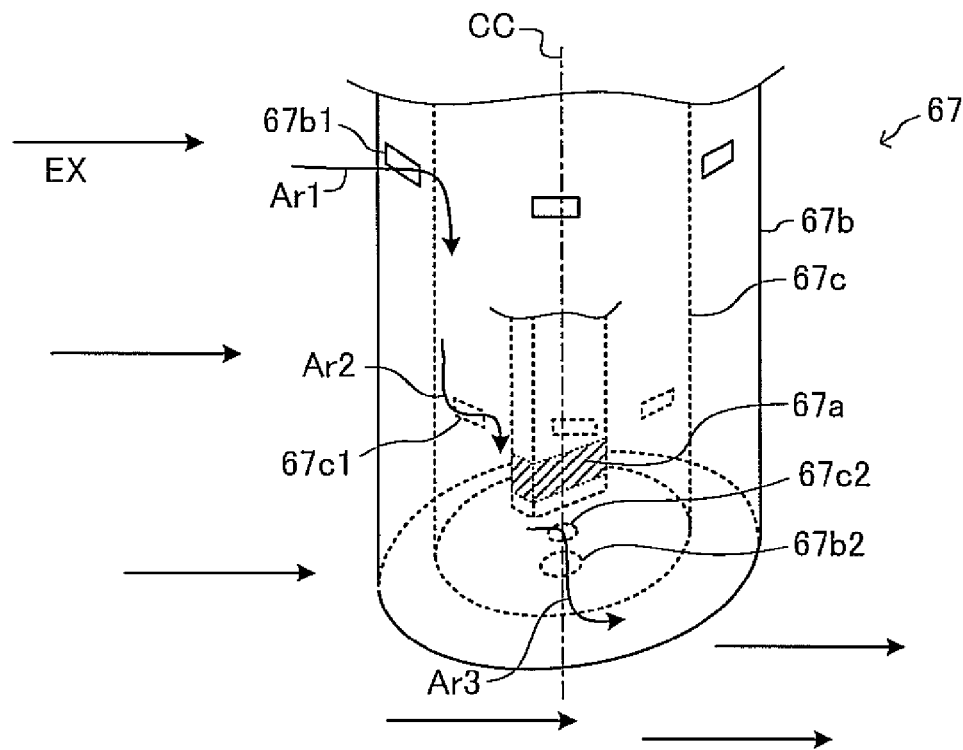
FIG. 8 is partial, schematic perspective view of the air-fuel ratio sensor (upstream-side air-fuel ratio sensor) shown in FIG. 1 and FIG. 7.
Figure 9:
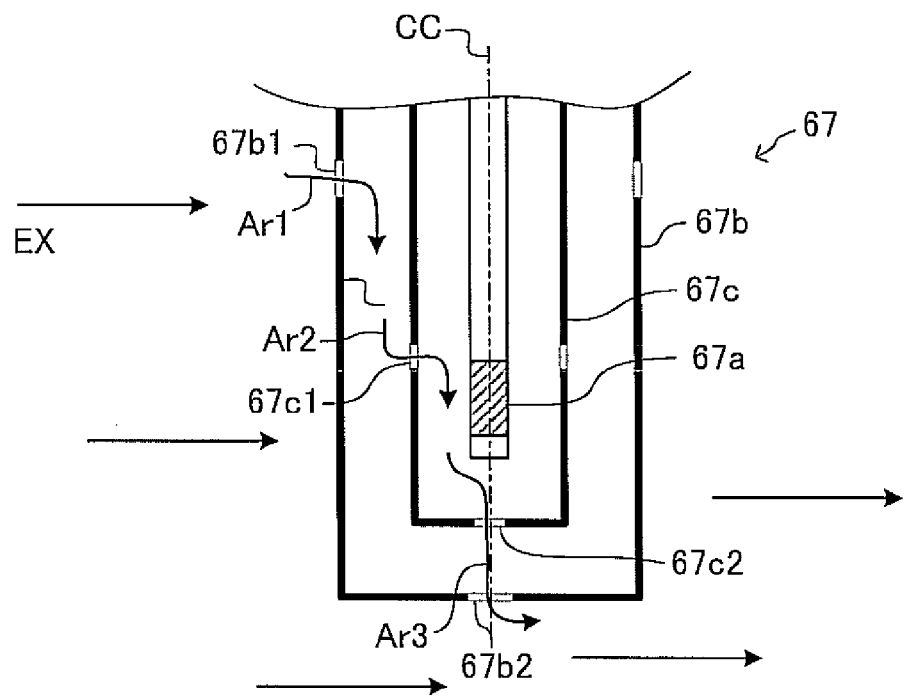
FIG. 9 is a partial sectional view of the air-fuel ratio sensor shown in FIG. 1 and FIG. 7.

As shown in FIGS. 8 and 9, the upstream-side air-fuel ratio sensor 67 comprises an air-fuel ratio detecting section 67a, an outer protective cover 67b, and an inner protective cover 67c.

The outer protective cover 67b has a hollow cylindrical body made of a metal. The outer protective cover 67b accommodates the inner protective cover 67c in its inside so as to cover the inner protective cover 67c. The outer protective cover 67b comprises a plurality of inflow holes 67b1 at its side surface. The inflow hole 67b1 is a through-hole which allows the exhaust gas EX (the exhaust gas outside of the outer protective cover 67b) passing through the exhaust gas passage to flow into the inside of the outer protective cover 67b. Further, the outer protective cover 67b has outflow holes 67b2 which allow the exhaust gas inside of the outer protective cover 67b to flow out to the outside (the exhaust gas passage) of the outer protective cover 67b, at a bottom surface of it.

The inner protective cover 67c is made of a metal and has a hollow cylindrical body having a diameter smaller than a diameter of the outer protective cover 67*b*. The inner protective cover 67*c* accommodates the air-fuel ratio detection section 67*a* in its inside so as to cover the air-fuel ratio detection section 67*a*. The inner protective cover 67*c* comprises a plurality of inflow holes 67*c*1 at its side surface. The inflow hole 67*c*1 is a through-hole which allows the exhaust gas flowing into "a space between the outer protective cover 67*b* and the inner protective cover 67*c*" through the inflow holes 67*b*1 of the outer protective cover 67*b* to further flow into the inside of the inner protective cover 67*c*. In addition, the inner protective cover 67*c* has outflow holes 67*c*2 which allow the exhaust gas inside of the inner protective cover 67*c* to flow out to the outside of the inner protective cover 67*c*, at a bottom surface of it.

Figure 2:
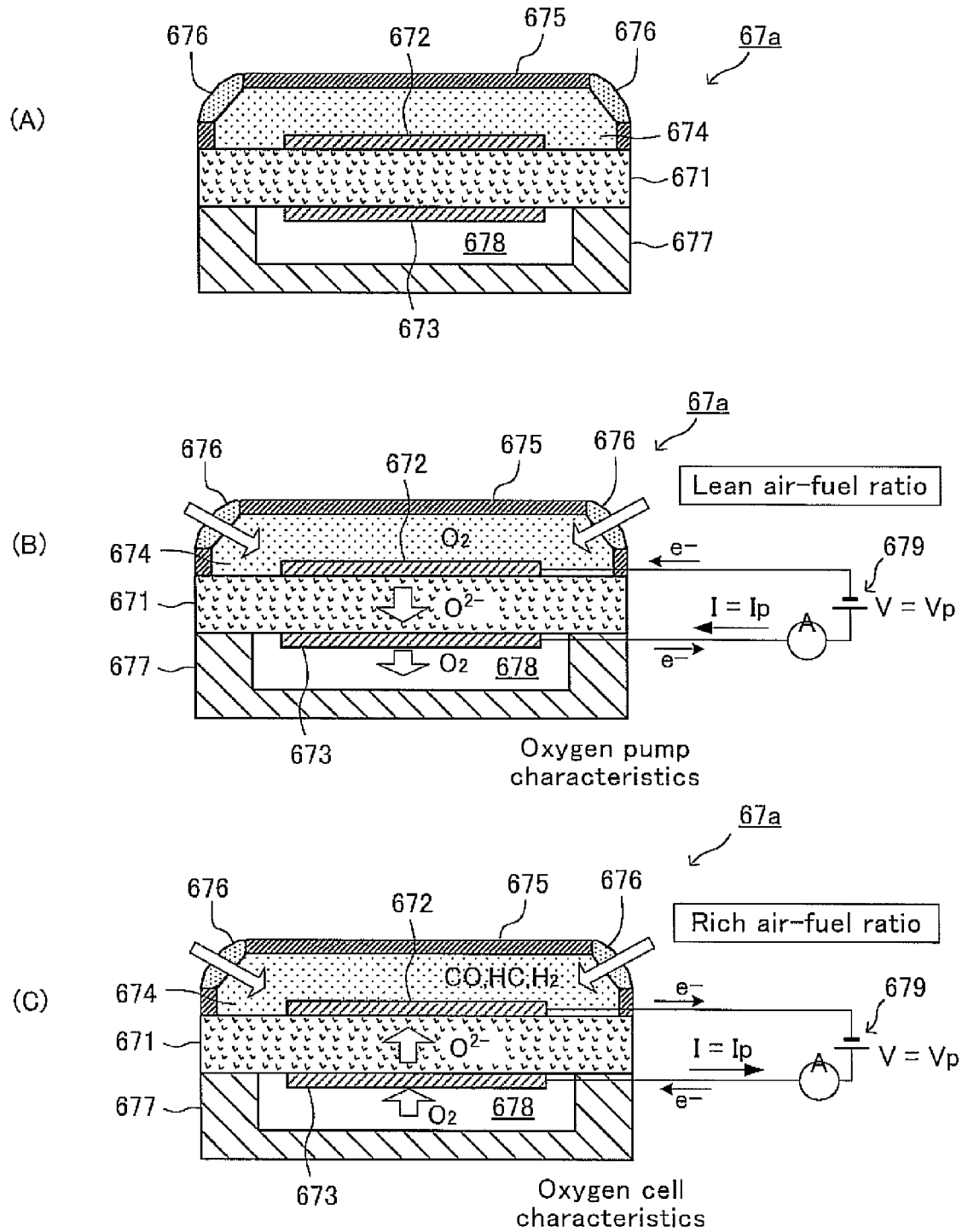
FIG. 2 includes (A)-(C), each showing a schematic sectional view of an air-fuel ratio detection section of an air-fuel ratio sensor (an upstream-side air-fuel ratio sensor) shown in FIG. 1.

As shown in (A)-(C) of FIG. 2, the air-fuel ratio detection section 67*a* includes a solid electrolyte layer 671, an exhaust-gas-side electrode layer 672, an atmosphere-side electrode layer 673, a diffusion resistance layer 674, a first wall section 675, a catalytic section 676, and a second wall section 677.

The solid electrolyte layer 671 is an oxide sintered body having oxygen ion conductivity. In the present example, the solid electrolyte layer 671 is "a stabilized zirconia element" in which CaO as a stabilizing agent is solid-solved in $ZrO_2$ (zirconia). The solid electrolyte layer 671 exerts the well-known "an oxygen cell characteristic" and "an oxygen pumping characteristic", when a temperature of the solid electrolyte layer 671 is higher than an activating temperature.

The exhaust-gas-side electrode layer 672 is made of a precious metal such as Platinum (Pt) which has a high catalytic activity. The exhaust-gas-side electrode layer 672 is formed on one of surfaces of the solid electrolyte layer 671. The exhaust-gas-side electrode layer 672 is formed by chemical plating and the like in such a manner that it has an adequately high permeability (i.e., it is porous).

The atmosphere-side electrode layer 673 is made of a precious metal such as Platinum (Pt) which has a high catalytic activity. The atmosphere-side electrode layer 673 is formed on the other one of surfaces of the solid electrolyte layer 671 in such a manner that it faces (opposes) to the exhaust-gas-side electrode layer 672 to sandwich the solid electrolyte layer 671 therebetween. The atmosphere-side electrode layer 673 is formed by chemical plating and the like in such a manner that it has an adequately high permeability (i.e., it is porous).

The diffusion resistance layer (diffusion rate-limiting layer) 674 is made of a porous ceramic (a heat resistant inorganic substance). The diffusion resistance layer 674 is formed so as to cover an outer surface of the exhaust-gas-side electrode layer 672 by, for example, plasma spraying and the like.

The first wall section 675 is made of a dense alumina ceramics through which gases can not pass. The first wall section 675 is formed so as to cover the diffusion resistance layer 674 except corners (portions) of the diffusion resistance layer 674. That is, the first wall section 675 has pass-through portions which expose portions of the diffusion resistance layer 674 to outside.

The catalytic section 676 is formed in the pass-through portions of the first wall section 675 so as to close the pass-through portions. The catalytic section 676 includes the catalytic substance which facilitates an oxidation-reduction reaction and a substance for storing oxygen which exerts the oxygen storage function, similarly to the upstream-side catalyst 53. The catalytic section 676 is porous. Accordingly, as shown by a white painted arrow in (B) and (C) of FIG. 2, the exhaust gas (the above described exhaust gas flowing into the inside of the inner protective cover 67*c*) reaches the diffusion resistance layer 674 through the catalytic section 676, and then further reaches the exhaust-gas-side electrode layer 672 through the diffusion resistance layer 674.

The second wall section 677 is made of a dense alumina ceramics through which gases can not pass. The second wall section 677 is configured so as to form "an atmosphere chamber 678" which is a space that accommodates the atmosphere-side electrode layer 673. An air is introduced into the atmosphere chamber 678.

An electric power supply 679 is connected to the upstream-side air-fuel ratio sensor 67. The electric power supply 679 applies an electric voltage V (=Vp) in such a manner that an electric potential of the atmosphere-side electrode layer 673 is higher than an electric potential of the exhaust-gas-side electrode layer 672.

Figure 3:
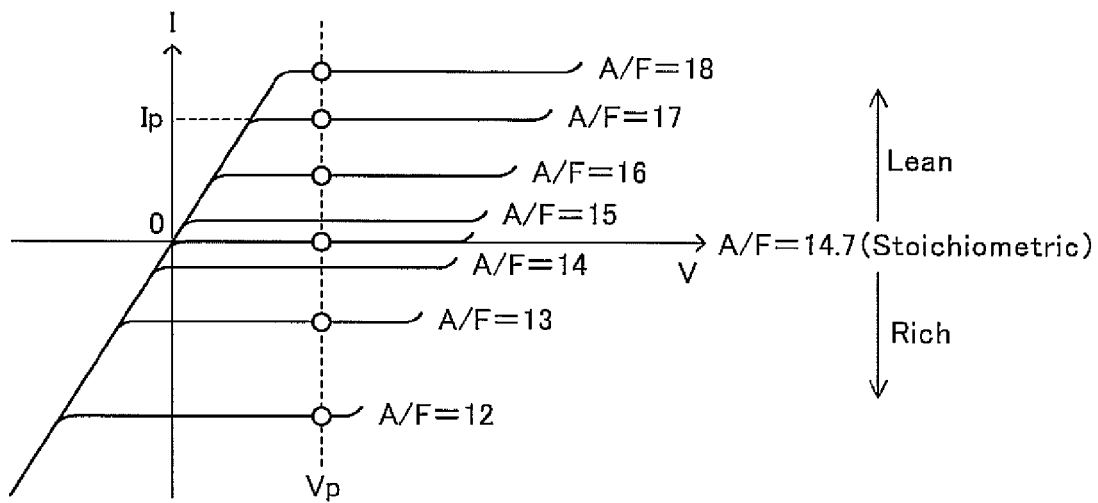
FIG. 3 is a graph showing a relationship between an air-fuel ratio of the exhaust gas and a limiting current value of the air-fuel ratio sensor.

As shown in (B) of FIG. 2, when the air-fuel ratio of the exhaust gas is leaner (larger) than the stoichiometric air-fuel ratio, the thus configured upstream-side air-fuel ratio sensor 67 ionizes oxygen which has reached the exhaust-gas-side electrode layer 672 through the diffusion resistance layer 674, and makes the ionized oxygen reach the atmosphere-side electrode layer 673. As a result, an electrical current I flows from a positive electrode of the electric power supply 679 to a negative electrode of the electric power supply 679. As shown in FIG. 3, the magnitude of the electrical current I becomes a constant value which is proportional to a concentration (or a partial pressure) of oxygen arriving at the exhaust-gas-side electrode layer 672 (an air-fuel ratio of the exhaust gas), when the electric voltage V is set at a predetermined value Vp or higher. The upstream-side air-fuel ratio sensor 67 outputs a value into which the electrical current (i.e., the limiting current Ip) is converted, as its output value Vabyfs.

To the contrary, as shown in (C) of FIG. 2, when the air-fuel ratio of the exhaust gas is richer (smaller) than the stoichiometric air-fuel ratio, the upstream-side air-fuel ratio sensor 67 ionizes oxygen existing in the atmosphere chamber 678 and makes the ionized oxygen reach the exhaust-gas-side electrode layer 672 so as to oxide the unburnt substances (HC, CO, and $H_2$ etc.) reaching the exhaust-gas-side electrode layer 672 through the diffusion resistance layer 674. As a result, an electrical current I flows from the negative electrode of the electric power supply 679 to the positive electrode of the electric power supply 679. As shown in FIG. 3, the magnitude of the electrical current I also becomes a constant value which is proportional to a concentration of the unburnt substances arriving at the exhaust-gas-side electrode layer 672 (an air-fuel ratio of the exhaust gas), when the electric voltage V is set at the predetermined value Vp or higher. The upstream-side air-fuel ratio sensor 67 outputs a value into which the electrical current (i.e., the limiting current Ip) is converted, as its output value Vabyfs.

Figure 4:
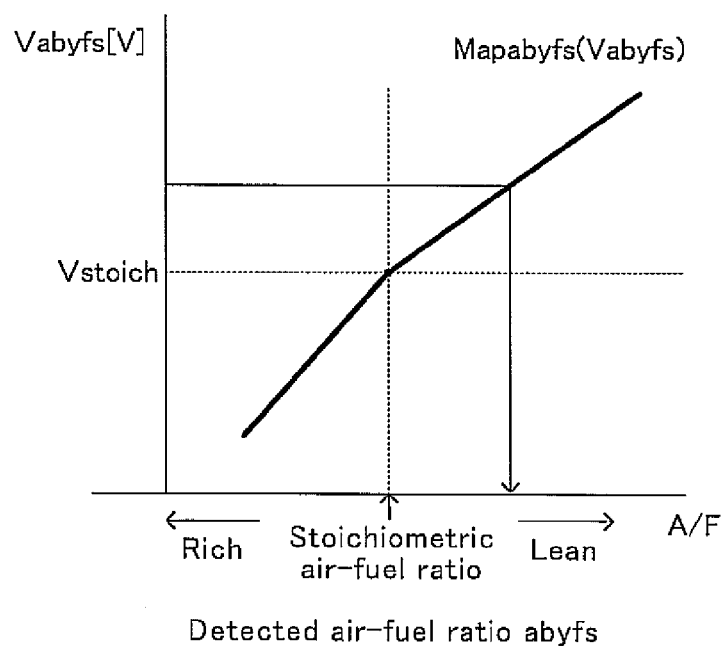
FIG. 4 is a graph showing a relationship between the air-fuel ratio of the exhaust gas and an output value of the air-fuel ratio sensor.

That is, the air-fuel detection section 67*a*, as shown in FIG. 4, outputs, as "an air-fuel ratio sensor output", the output value Vabyfs in accordance with the air-fuel ratio (an upstream-side air-fuel ratio abyfs, a detected air-fuel ratio abyfs) of the gas, the gas flowing at the position at which the upstream-side air-fuel ratio sensor 67 is disposed and reaching the air-fuel detection section 67*a* through the inflow holes 67*b*1 of the outer protective cover 67*b* and the inflow holes 67*c*1 of the inner protective cover 67*c*. The output value Vabyfs becomes larger as the air-fuel ratio of the gas reaching the air-fuel ratio detection section 67*a* becomes larger (leaner). That is, the output value Vabyfs is substantially proportional to the air-fuel ratio of the exhaust gas reaching the air-fuel ratio detection section 67*a*. It should be noted that the output value Vabyfs becomes equal to a stoichiometric air-fuel ratio corresponding value Vstoich, when the detected air-fuel ratio abyfs is equal to the stoichiometric air-fuel ratio.

The electric controller 70 stores an air-fuel ratio conversion table (map) Mapabyfs shown in FIG. 4, and detects an actual upstream-side air-fuel ratio abyfs (that is, obtains the detected air-fuel ratio abyfs) by applying an actual output value Vabyfs of the air-fuel ratio sensor 67 to the air-fuel ratio conversion table Mapabyfs.

Meanwhile, the upstream-side air-fuel ratio sensor 67 is disposed in such a manner that the outer protective cover 67b is exposed in either the exhaust manifold 51 or the exhaust pipe 52 at the position between the exhaust-gas-aggregated-portion (exhaust gas merging portion) HK of the exhaust manifold 51 and the upstream-side catalyst 53.

Specifically, as shown in FIGS. 8 and 9, the air-fuel ratio sensor 67 is disposed in the exhaust gas passage in such a manner that a bottom surface of the protective cover (67b, 67c) is parallel to a flow of the exhaust gas EX, and a center line CC of the protective cover (67b, 67c) is orthogonal to the flow of the exhaust gas EX. This causes the exhaust gas EX reaching the inflow holes 67b1 of the outer protective cover 67b in the exhaust gas passage to be introduced into the outer protective cover 67b and the inner protective cover 67c owing to a flow of the exhaust gas EX flowing in the vicinity of the outflow holes 67b2 of the outer protective cover in the exhaust gas passage.

Accordingly, the exhaust gas EX flowing through the exhaust gas passage flows into a space between the outer protective cover 67b and the inner protective cover 67c via inflow holes 67b1 of the outer protective cover 67b, as shown by an arrow Ar1 in FIGS. 8 and 9. Subsequently, the exhaust gas, as shown by an arrow Ar2, flows into "an inside of the inner protective cover 67c" through "inflow holes 67c1 of the inner protective cover 67c", and thereafter, reaches the air-fuel ratio detection section 67a. Then, the exhaust gas flows out to the exhaust gas passage through "the outflow holes 67c2 of the inner protective cover 67c and the outflow holes 67b2 of the outer protective cover 67b", as shown by an arrow Ar3.

Accordingly, a flow rate of the exhaust gas inside of "the outer protective cover 67b and the inner protective cover 67c" varies depending on a flow rate of the exhaust gas EX flowing in the vicinity of the outflow holes 67b2 of the outer protective cover 67b (and therefore, depending on the intake air flow rate Ga which is the intake air amount per unit time). In other words, a time period from "a timing when an exhaust gas (a first exhaust gas) having a certain air-fuel ratio reaches the outflow hole 67b1" to "a timing when the first exhaust gas reaches the air-fuel ratio detection section 67a" varies depending on the intake air flow rate Ga, but does not vary depending on the engine rotational speed NE. Accordingly, the output responsivity of the air-fuel ratio sensor 67 with respect to "the air-fuel ratio of the exhaust gas flowing through the exhaust gas passage" becomes better as an flow amount (a flow rate) of the exhaust gas flowing in the vicinity of the outer protective cover 67b of the air-fuel ratio sensor 67. This is also true when the upstream-side air fuel ratio sensor 67 comprises the inner protective cove 67 only.

Referring back to FIG. 7 again, the downstream-side air-fuel ratio sensor 68 is disposed in the exhaust pipe 52 and at a position downstream of the upstream-side catalyst 53 and upstream of the downstream-side catalyst (that is, in the exhaust gas passage between the upstream-side catalyst 53 and the downstream-side catalyst). The downstream-side air-fuel ratio sensor 68 is a well-known electromotive-force-type oxygen concentration sensor (concentration-cell-type well-known oxygen sensor utilizing a stabilized zirconia). The downstream-side air-fuel ratio sensor 68 outputs an output value Voxs in accordance with an air-fuel ratio of a gas to be detected, the gas passing through a position at which the downstream-side air-fuel ratio sensor 68 is disposed (i.e., the value Voxs in accordance with an air-fuel ratio of a gas flowing out from the upstream-side catalyst 53 and flowing into the downstream-side catalyst, and therefore, in accordance with a time mean value of an air-fuel ratio of the mixture supplied to the engine).

Figure 10:
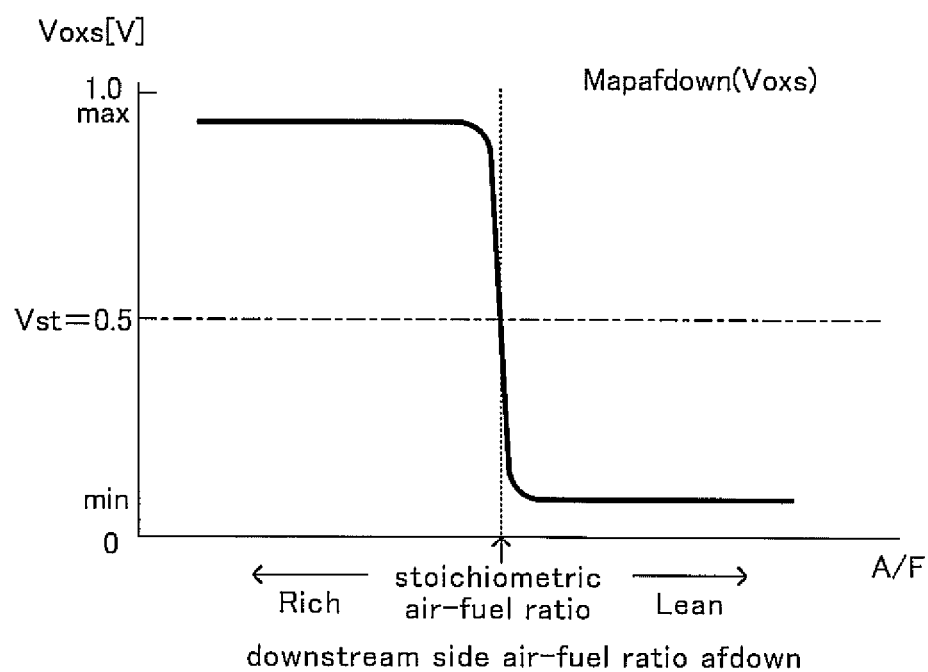
FIG. 10 is a graph showing a relationship between the air-fuel ratio of the exhaust gas and an output value of a downstream-side air-fuel ratio sensor shown in FIG. 1 and FIG. 7.

As shown in FIG. 10, the output value Voxs becomes equal to a maximum output value max (e.g., about 0.9 V) when the air-fuel ratio of the gas to be detected is richer than the stoichiometric air-fuel ratio, becomes equal to a minimum output value min (e.g., about 0.1 V) when the air-fuel ratio of the gas to be detected is leaner than the stoichiometric air-fuel ratio, and becomes equal to a voltage Vst which is about a middle value between the maximum output value max and the minimum output value min (the middle voltage Vst, e.g., about 0.5 V) when the air-fuel ratio of the gas to be detected is equal to the stoichiometric air-fuel ratio. Further, the output value Voxs varies rapidly from the maximum output value max to the minimum output value min when the air-fuel ratio of the gas to be detected varies from the air-fuel ratio richer than the stoichiometric air-fuel ratio to the air-fuel ratio leaner than the stoichiometric air-fuel ratio, and the output value Voxs varies rapidly from the minimum output value min to the maximum output value max when the air-fuel ratio of the gas to be detected varies from the air-fuel ratio leaner than the stoichiometric air-fuel ratio to the air-fuel ratio richer than the stoichiometric air-fuel ratio.

The accelerator opening sensor 69 shown in FIG. 7 outputs a signal representing an operation amount Accp (an accelerator pedal operation amount Accp) of the accelerator pedal 81 operated by a driver. The accelerator pedal operation amount Accp increases as an opening angle (the accelerator pedal operation amount) of the accelerator pedal 81 becomes larger.

The electric controller 70 is a well-known microcomputer, which includes the following mutually bus-connected elements: "a CPU 71; ROM 72 in which programs to be executed by the CPU 71, tables (maps, functions), constants, and the like are stored in advance; RAM 73 in which the CPU 71 temporarily stores data as needed; backup RAM 74; an interface 75 including an AD converter, and so on".

The backup RAM 74 is configured in such a manner that it is supplied with an electric power from a battery of a vehicle on which the engine 10 is mounted regardless of a position (any one of an off-position, a start-position, an on-position, and the like) of an ignition key switch of the vehicle. The backup RAM 74 stores data (data is written into the backup RAM 74) in accordance with an instruction from the CPU 71 and retains (stores) the stored data in such a manner that the data can be read out, while it is supplied with the electric power from the battery. The backup RAM 74 can not retain the data, while supplying the electric power from the battery is stopped, such as when the battery is taken out from the vehicle. Accordingly, the CPU 71 initializes data to be stored in the backup RAM 74 (or sets the data at default values), when supplying the electric power to the backup RAM 74 is resumed.

The interface 75 is connected to the sensors 61 to 69 and supplies signals from the sensors to the CPU 71. Further, the interface 75 sends drive signals (instruction signals), in accordance to instructions from the CPU 71, to each of the actuator 33a of the variable intake timing control unit 33, the actuator 36a of the variable exhaust timing control unit 36, each of the igniters 38 of each of the cylinders, each of the fuel injectors 39 provided corresponding to each of the cylinders, the throttle valve actuator 44a, etc.

It should be noted that the electric controller 70 sends the instruction signal to the throttle valve actuator 44a, in such a manner that the throttle valve opening angle TA is increased as the obtained accelerator pedal operation amount Accp becomes larger. That is, the electric controller 70 comprises throttle valve driving means for varying the opening angle of "the throttle valve 44 disposed in the intake passage of the engine 10" in accordance with an acceleration operation amount (the accelerator pedal operation amount Accp) of the engine 10 changed by the driver.

(Outline of a Determination of an Air-Fuel Ratio Imbalance Among Cylinders)

Next will be described the outline of the determination of an air-fuel ratio imbalance among cylinders, which is adopted by the first determining apparatus. The determination of an air-fuel ratio imbalance among cylinders is a determination for determining whether or not the air-fuel ratio imbalance among cylinders becomes larger than a warning value, due to a change in a performance characteristic of the fuel injector 39, and the like. In other words, the first determining apparatus determines that the air-fuel ratio imbalance (state) among cylinders has been occurring, if the difference (the difference between individual cylinder air-fuel-ratios) between the imbalance cylinder air-fuel ratio and the un-imbalance (normal) cylinder air-fuel ratio is larger than or equal to "a degree which can not be admissible in terms of the emission"

The first determining apparatus, in order to perform the determination of an air-fuel ratio imbalance among cylinders, obtains "a variation amount per unit time (a constant sampling time ts)" of "the air-fuel ratio represented by the output value Vabyfs of the air-fuel ratio sensor 67 (i.e., the detected air-fuel ratio abyfs obtained by applying the output value Vabyfs to the air-fuel ratio conversion table Mapabyfs shown in FIG. 4)". This "variation amount per unit time of the detected air-fuel ratio abyfs" can be referred to as a differential value d(abyfs)/dt with respect to time of the detected air-fuel ratio abyfs, when the unit time is an extremely short time such as 4 m seconds. Accordingly, "the variation amount per unit time of the detected air-fuel ratio abyfs" is also referred to as "a detected air-fuel ratio changing rate $\Delta AF$".

The exhaust gas from each of the cylinders reaches the air-fuel ratio sensor 67 in order of ignition (and thus, in order of exhaust). When the air-fuel ratio imbalance among cylinders is not occurring, the air-fuel ratio of the exhaust gas, discharged from each of the cylinders and reaching the air-fuel ratio sensor 67, is substantially equal to each other. Accordingly, for example, the detected air-fuel ratio abyfs varies as shown by a dotted line C1 in (B) of FIG. 5, when the air-fuel ratio imbalance among cylinders is not occurring. That is, when the air-fuel ratio imbalance among cylinders is not occurring, the wave shape of the output value Vabyfs of the air-fuel ratio sensor 67 is substantially flat. Accordingly, as shown by a dotted line C3 in (C) of FIG. 5, an absolute value of the detected air-fuel ratio changing rate $\Delta AF$ is small, when the air-fuel ratio imbalance among cylinders is not occurring.

To the contrary, when a characteristic of "the fuel injector 39 for injecting the fuel to a specific cylinder (e.g., the first cylinder)" becomes a characteristic that "the injector injects a greater amount of or a shorter amount of fuel compared to the instructed fuel injection amount", and thus the air-fuel ratio imbalance (state) among cylinders occurs, an air-fuel ratio (the imbalance cylinder air-fuel ratio) of an exhaust gas from the specific cylinder differs greatly from an air-fuel ratio (the un-imbalance cylinder air-fuel ratio) of an exhaust gas from a cylinder other than the specific cylinder.

Figure 5:
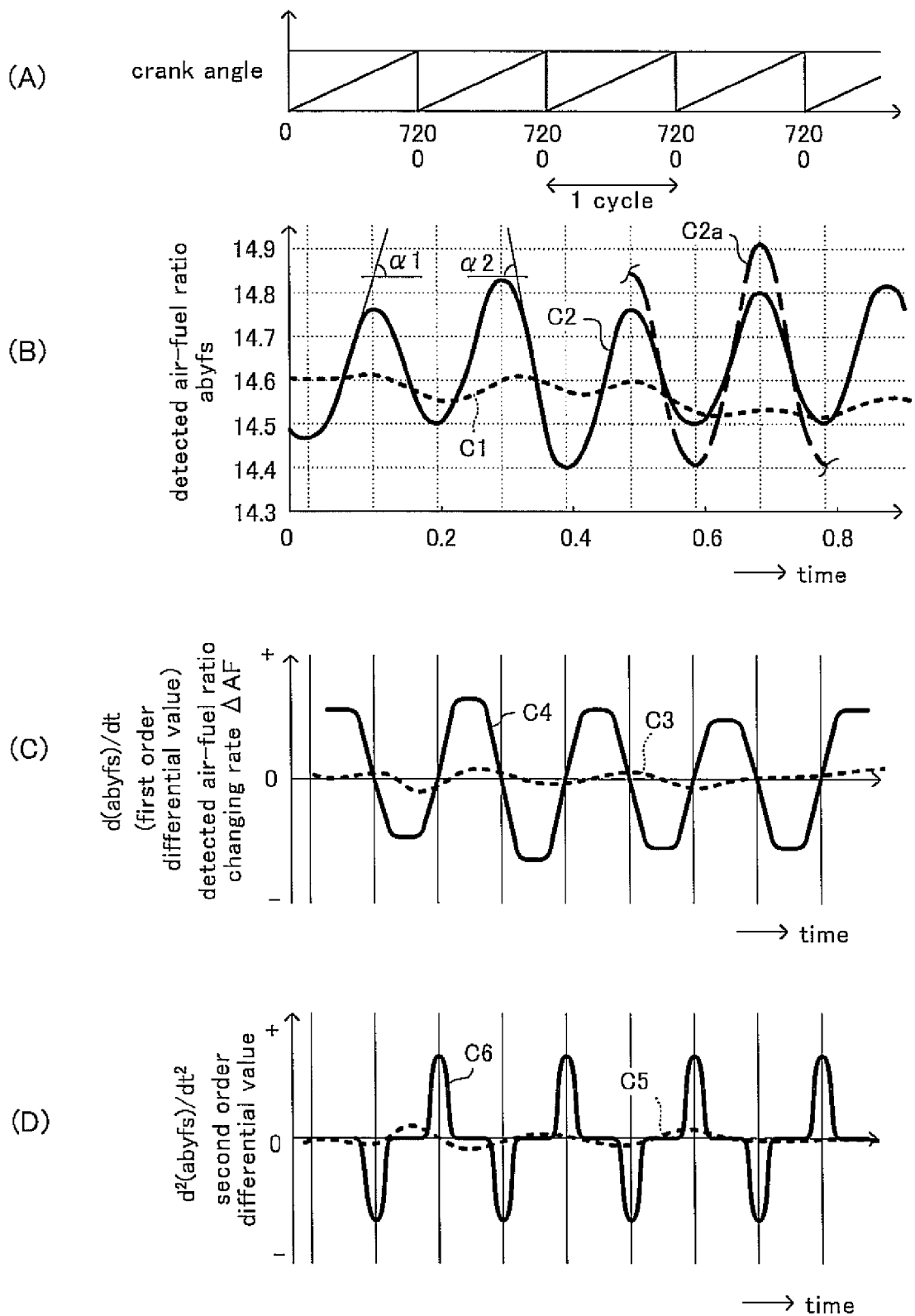
FIG. 5 is a timing chart showing behaviors of various values relating to a parameter for imbalance determination, when an air-fuel ratio imbalance (state) among cylinders is occurring and is not occurring.

Accordingly, for example, as shown by a solid line C2 in (B) of FIG. 5, the detected air-fuel ratio abyfs when the air-fuel ratio imbalance (state) among cylinders is occurring varies greatly every unit combustion cycle period. The absolute value of the detected air-fuel ratio changing rate AF is therefore large when the air-fuel ratio imbalance among cylinders is occurring, as shown by a solid line C4 in (C) of FIG. 5. It should be noted that the unit combustion cycle period for the 4 cycle and 4 cylinder engine 10 corresponds to a period for which 720° crank angle passes, that is, a period for which a certain crank angle passes, the certain crank angle necessary for each of the cylinders (the first to fourth cylinder) to complete a single combustion stroke, each of the cylinders discharging an exhaust gas which reaches the single air-fuel ratio sensor 67.

Further, the absolute value $|\Delta AF|$ of the detected air-fuel ratio changing rate $\Delta AF$ varies more greatly, as the air-fuel ratio of the imbalance cylinder deviates more greatly from the air-fuel ratio of the un-imbalance cylinder. For example, assuming that the detected air-fuel ratio abyfs varies as shown by the solid line C2 in (B) of FIG. 5 when the magnitude (absolute value) of the difference between the air-fuel ratio of the imbalance cylinder and the air-fuel ratio of the un-imbalance cylinder is a first value, the detected air-fuel ratio abyfs varies as shown by the alternate long and short dash line C2a in (B) of FIG. 5 when the magnitude (absolute value) of the difference between the air-fuel ratio of the imbalance cylinder and the air-fuel ratio of the un-imbalance cylinder is "a second value larger than the first value". Accordingly, the absolute value of the detected air-fuel ratio changing rate $\Delta AF$ becomes larger as the air-fuel ratio of the imbalance cylinder deviates (differs) more greatly from the air-fuel ratio of the un-imbalance cylinder.

In view of the above, the first determining apparatus obtains the detected air-fuel ratio changing rate $\Delta AF$ (a first order differential value d(abyfs)/dt) as a basic indicative value every time the sampling time is passes (elapses) in a single unit combustion cycle period. The first determining apparatus obtains a mean (average) value of the absolute values $|\Delta AF|$ of the detected air-fuel ratio changing rates $\Delta AF$, the absolute values having been obtained multiple times in the single unit combustion cycle period. Thereafter, the first determining apparatus obtains a mean (average) value of "the mean value of the absolute values $|\Delta AF|$ of the detected air-fuel ratio changing rates $\Delta AF$", each of the absolute values $|\Delta AF|$ having been obtained for each of a plurality of the unit combustion cycle periods. The first determining apparatus adopts the obtained mean value of the mean value of the absolute values $|\Delta AF|$ as the air-fuel-ratio-variation-indicative-value AFD, and adopts the air-fuel-ratio-variation-indicative-value as a parameter X for imbalance determination. It should be noted that the parameter X for imbalance determination is not limited to the value described above, but can be obtained using various ways described later.

The first determining apparatus sets a target air-fuel ratio abyfr which is a target value of the air-fuel ratio of the engine to (at) "a target rich air-fuel ratio AFrich other than the stoichiometric air-fuel ratio" in a period in which (while) it obtains the detected air-fuel ratio changing rates $\Delta AF$ which is a basic data for the air-fuel-ratio-variation-indicative-value AFD (parameter X for imbalance determination). The target rich air-fuel ratio AFrich is an air-fuel ratio in a region richer than the stoichiometric air-fuel ratio (e.g., 14.6). That is, the target rich air-fuel ratio AFrich is an air-fuel ratio smaller than the stoichiometric air-fuel ratio by a certain amount, and may be, for example, 14.0. The target rich air-fuel ratio AFrich is one of "non-stoichiometric air-fuel ratios to be set as the target air-fuel ratios". It should be noted that the first determining apparatus may adopt, as one of the non-stoichiometric air-fuel ratios, "a target lean air-fuel ratio AFlean (which is larger than the stoichiometric air-fuel ratio by a certain amount, and may be, for example, 15.2) which is an air-fuel ratio in a region leaner than the stoichiometric air-fuel ratio".

As described above, when the target air-fuel ratio abyfr is set at the target rich air-fuel ratio AFrich, the air-fuel ratio of the engine fluctuate (varies) in the vicinity of the target rich air-fuel ratio AFrich. Accordingly, an oxidation reaction continues at the exhaust-gas-side electrode layer 672 of the air-fuel ratio sensor 67. In other words, a reaction at the exhaust-gas-side electrode layer 672 does not change frequently "from the oxidation reaction to a reduction reaction, and vice versa", unlike a reaction observed when the target air-fuel ratio abyfr is set at the stoichiometric air-fuel ratio. A responsivity of the air-fuel ratio sensor 67 is therefore excellent. As a result, the first determining apparatus can obtain the parameter X for imbalance determination under a condition in which the responsivity of the air-fuel ratio sensor is not low or poor. Accordingly, the parameter X for imbalance determination obtained by the first determining apparatus represents (or is indicative of) the degree of the air-fuel ratio imbalance (state) among cylinders (the difference between individual cylinder air-fuel-ratios) with high accuracy.

The first determining apparatus obtains the parameter X for imbalance determination, and then compares the parameter X for imbalance determination with a threshold value Xth for imbalance determination. The first determining apparatus determines that the air-fuel ratio imbalance (state) among cylinders is occurring when the parameter X for imbalance determination is larger than the threshold value Xth for imbalance determination. To the contrary, the first determining apparatus determines that the air-fuel ratio imbalance (state) among cylinders is not occurring when the parameter X for imbalance determination is smaller than the threshold value Xth for imbalance determination. This is the principle that the first determining apparatus adopts for the determination of the air-fuel ratio imbalance among cylinders.

(Actual Operation)
<Fuel Injection Amount Control>

The CPU 71 of the first determining apparatus repeatedly executes "a routine to calculate an instructed fuel injection amount Fi and instruct an fuel injection" shown by a flowchart in FIG. 11, every time the crank angle of each of the cylinders reaches a predetermined crank angle before its intake top dead center (e.g., BTDC 90° CA), for the cylinder whose crank angle has reached the predetermined crank angle (hereinafter, referred to as "a fuel injection cylinder"). Accordingly, at an appropriate timing, the CPU 71 starts a process from step 1100, and proceeds to step 1110 to determine whether or not a fuel cut condition (hereinafter, expressed as "a FC condition") is satisfied.

Assuming that the FC condition is not satisfied, the CPU 71 makes a "No" determination to proceed to step 1120 at which the CPU 71 obtains "a cylinder intake air amount Mc(k)" which is "an air amount introduced into the fuel injection cylinder", on the basis of "the intake air flow rate Ga measured by the air-flow meter 61, the engine rotational speed NE obtained based on the signal from the crank position sensor 64, and a look-up table MapMc". The cylinder intake air amount Mc(k) is stored in the RAM, while being related to the intake stroke of each cylinder. The cylinder intake air amount Mc(k) may be calculated based on a well-known air model (a model constructed according to laws of physics describing and simulating a behavior of an air in the intake passage).

Subsequently, the CPU 71 determines whether or not a value of a forced air-fuel-ratio-shift flag Xyose is "0". The value of the forced air-fuel-ratio-shift flag Xyose is set at "0" in an initialization routine. The initialization routine is executed when the ignition key switch of the vehicle on which the engine 10 is mounted is turned on from off. The value of the forced air-fuel-ratio-shift flag Xyose is set to (at) "1" in a routine shown in FIG. 14 described later, when a predetermined condition(s) is/are satisfied (i.e., when it is determined that a forced air-fuel-ratio-shift-control should be performed).

Here, it is assumed that the value of the forced air-fuel-ratio-shift flag Xyose is "0". In this case, the CPU 71 makes a "Yes" determination at step 1130 to perform processes from step 1140 to step 1170 described below. Thereafter, the CPU 71 proceeds to step 1195 to end the present routine tentatively.

Step 1140: the CPU 71 sets the target air-fuel ratio abyfr (the target upstream-side air-fuel ratio abyfr) to (at) the stoichiometric air-fuel ratio stoich (e.g., 14.6).

Step 1150: the CPU 71 obtains a base fuel injection amount Fbase by dividing the cylinder intake air amount Mc(k) by the target air-fuel ratio abyfr. Accordingly, the base fuel injection amount Fbase is a feedforward amount of the fuel injection amount required to realize the target air-fuel ratio abyfr. The step 1150 constitutes feedforward control means (air-fuel ratio control means) to have the air-fuel ratio of a mixture supplied to the engine become equal to the target air-fuel ratio abyfr.

Step 1160: the CPU 71 corrects the base fuel injection amount Fbase with a main feedback amount DFi. More specifically, the CPU 71 calculates the instructed fuel injection amount (a final fuel injection amount) Fi by adding the main feedback amount DFi to the base fuel injection amount Fbase. The main feedback amount DFi is an air-fuel ratio feedback amount to have the air-fuel ratio of the engine coincide with the target air-fuel ratio abyfr. The way in which the main feedback amount DFi is calculated is described later.

Step 1170: the CPU 71 sends a fuel injection instruction signal to "the injector 39 disposed so as to correspond to the fuel injection cylinder" in order to have the injector 39 inject "a fuel of the instructed fuel injection amount Fi".

Consequently, the fuel whose amount is required to have the air-fuel ratio of the engine coincide with the stoichiometric air-fuel ratio is injected from the fuel injector 39 of the fuel injection cylinder. That is, the steps from 1150 to 1170 constitute instructed fuel injection amount control means for controlling the instructed fuel injection amount Fi in such a manner that "the air-fuel ratio of the mixtures supplied to the combustion chambers 25 of two or more of the cylinders (all of the cylinders in the present example) discharging the exhaust gases which reach the air-fuel ratio sensor 67" becomes equal to the target air-fuel ratio abyfr.

In the meantime, if the value of the forced air-fuel-ratio-shift flag Xyose is "1" when the CPU 71 performs the process of the step 1130, the CPU 71 makes a "No" determination at step 1130 to proceed to step 1180 to set the target air-fuel ratio abyfr set to (at) the target rich air-fuel ratio AFrich described above. The target rich air-fuel ratio AFrich is, for example, 14.0, and one of "the non-stoichiometric air-fuel ratios" described above.

It should be noted that the CPU 71 may set the target air-fuel ratio abyfr to (at) the target lean air-fuel ratio AFlean (which is an air-fuel ratio larger than the stoichiometric air-fuel ratio by a certain amount, and is, for example, 15.2). The target lean air-fuel ratio AFlean is also one of "the non-stoichiometric air-fuel ratios" described above.

Subsequently, the CPU 71 executes processes of the steps from 1150 to 1170, described above. As a result, when the characteristics of the fuel injectors 39 is normal, the fuel, whose amount is required to have the air-fuel ratio of the engine become equal to "the non-stoichiometric air-fuel ratio which is the target rich air-fuel ratio AFrich (or the target lean air-fuel ratio AFlean)", is injected from the injector 39 of the fuel injection cylinder.

It should be noted that, if the FC condition is satisfied when the CPU 71 executes the process of the step 1110, the CPU 71 makes a "Yes" determination to directly proceed to step 1195 at which CPU 71 ends the present routine tentatively. In this case, the fuel injection by the process of the step 1170 is not carried out, and a fuel cut control (fuel supply stopping control) is therefore performed.

<Calculation of the Main Feedback Amount>

Figure 12:
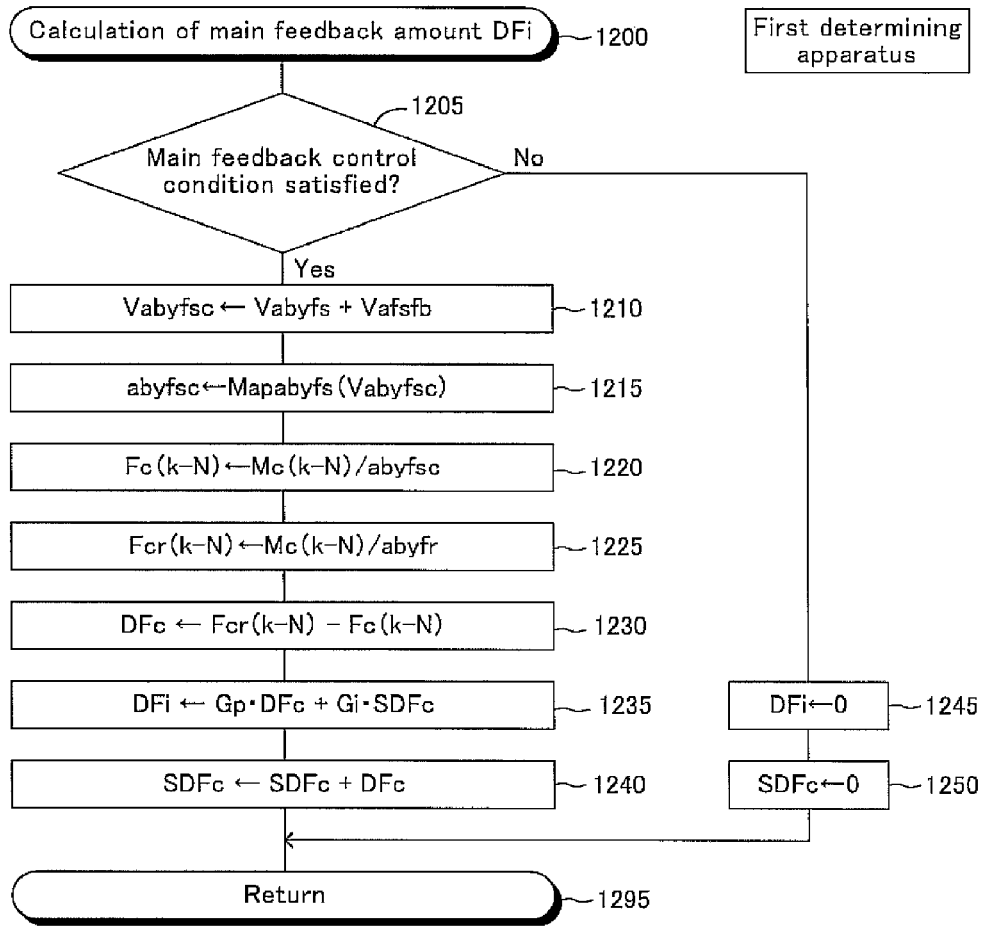
FIG. 12 is a flowchart showing a routine executed by the CPU of the first determining apparatus.

The CPU 71 repeatedly executes "a routine for the calculation of the main feedback amount" shown by a flowchart in FIG. 12, every time a predetermined time period elapses. Accordingly, at a predetermined timing, the CPU 71 starts the process from step 1200 to proceed to step 1205 at which CPU 71 determines whether or not "a main feedback control condition (an upstream-side air-fuel ratio feedback control condition)" is satisfied.

The main feedback control condition is satisfied when all of the following conditions are satisfied.
(A1) The air-fuel ratio sensor 67 has been activated.
(A2) The load (load rate) KL of the engine is smaller than or equal to a threshold value KLth.
(A3) The fuel cut control is not being performed.

It should be noted that the load rate KL is obtained based on the following formula (1). The accelerator pedal operation amount Accp can be used instead of the load rate KL. In the formula (1), Mc is the cylinder intake air amount, $\rho$ is an air density (unit is (g/l), L is a displacement of the engine 10 (unit is (l)), and "4" is the number of cylinders of the engine 10.

$$KL = (Mc/(\rho \cdot L/4)) \cdot 100\% \tag{1}$$

The description continues assuming that the main feedback control condition is satisfied. In this case, the CPU 71 makes a "Yes" determination at step 1205 to execute processes from steps 1210 to 1240 described below in this order, and then proceed to step 1295 to end the present routine tentatively.

Step 1210: The CPU 71 obtains an output value Vabyfsc for a feedback control, according to a formula (2) described below. In the formula (2), Vabyfs is the output value of the air-fuel ratio sensor 67, and Vafsfb is a sub feedback amount calculated based on the output value Voxs of the downstream side air-fuel ratio sensor 68. The way in which the sub feedback amount Vafsfb is calculated is well known. For example, the sub feedback amount Vafsfb is decreased when the output value Voxs of the downstream side air-fuel ratio sensor 68 is a value representing an richer air-fuel ratio compared to the value Vst which corresponds to the stoichiometric air-fuel ratio, and is increased when the output value Voxs of the downstream side air-fuel ratio sensor 68 is a value representing an leaner air-fuel ratio compared to the value Vst which corresponds to the stoichiometric air-fuel ratio. The first determining apparatus may not perform a sub feedback control by setting the sub feedback amount Vafsfb at "0".

$$Vabyfsc = Vabyfs + Vafsfb \tag{2}$$

Step 1215: The CPU 71 obtains an air-fuel ratio abyfsc for a feedback control by applying the output value Vabyfsc for a feedback control to the table Mapabyfs shown in FIG. 4, as shown by a formula (3) described below.

$$abyfsc = Mapabyfs(Vabyfsc) \tag{3}$$

Step 1220: According to a formula (4) described below, the CPU 71 obtains "a cylinder fuel supply amount Fc(k−N)" which is "an amount of the fuel actually supplied to the combustion chamber 25 for a cycle at a timing N cycles before the present time". That is, the CPU 71 obtains the cylinder fuel supply amount Fc(k−N) through dividing "the cylinder intake air amount Mc(k−N) which is the cylinder intake air amount for the cycle the N cycles (i.e., N·720° crank angle) before the present time" by "the air-fuel ratio abyfsc for a feedback control".

$$Fc(k-N) = Mc(k-N)/abyfsc \tag{4}$$

The reason why the cylinder intake air amount Mc(k−N) for the cycle N cycles before the present time is divided by the air-fuel ratio abyfsc for a feedback control in order to obtain the cylinder fuel supply amount Fc(k−N) is because "the exhaust gas generated by the combustion of the mixture in the combustion chamber 25" requires time "corresponding to the N cycles" to reach the air-fuel ratio sensor 67.

Step 1225: The CPU 71 obtains "a target cylinder fuel supply amount Fcr(k−N)" which is "a fuel amount supposed to be supplied to the combustion chamber 25 for the cycle the N cycles before the present time", according to a formula (5) described below. That is, the CPU 71 obtains the target cylinder fuel supply amount Fcr(k−N) by dividing the cylinder intake air amount Mc(k−N) for the cycle the N cycles before the present time by the target air-fuel ratio abyfr (=stoich or AFrich).

$$Fcr(k-N) = Mc(k-N)/abyfr \tag{5}$$

Step 1230: The CPU 71 obtains "an error DFc of the cylinder fuel supply amount", according to a formula (6) described below. That is, the CPU 71 obtains the error DFc of the cylinder fuel supply amount by subtracting the cylinder fuel supply amount Fc(k−N) from the target cylinder fuel supply amount Fcr(k−N). The error DFc of the cylinder fuel supply amount represents excess and deficiency of the fuel supplied to the cylinder the N cycle before the present time.

$$DFc = Fcr(k-N) - Fc(k-N) \tag{6}$$

Step 1235: The CPU 71 obtains the main feedback amount DFi, according to a formula (7) described below. In the formula (7) below, Gp is a predetermined proportion gain, and Gi is a predetermined integration gain. Further, "a value SDFc" in the formula (7) is "an integrated value of the error DFc of the cylinder fuel supply amount". That is, the CPU 71 calculates "the main feedback amount DFi" based on a proportional-integral control to have the air-fuel ratio abyfsc for a feedback control coincide with the target air-fuel ratio abyfr.

$$DFi = Gp \cdot DFc + Gi \cdot SDFc \tag{7}$$

Step 1240: The CPU 71 obtains a new integrated value SDFc of the error DFc of the cylinder fuel supply amount by adding the error DFc of the cylinder fuel supply amount obtained at the step 1230 to the current integrated value SDFc of the error DFc of the cylinder fuel supply amount.

As described above, the main feedback amount DFi is obtained based on the proportional-integral control. The main feedback amount DFi is reflected in (onto) the instructed fuel injection amount Fi by the process of the step 1160 in FIG. 11.

To the contrary, if the feedback condition is not satisfied at the time of determination at step 1205 in FIG. 12, the CPU 71 makes a "No" determination to proceed to step 1245 to set the value of the main feedback amount DFi at "0". Subsequently, the CPU 71 stores "0" into the integrated value SDFc of the error of the cylinder fuel supply amount at step 1250. Thereafter, the CPU 71 proceeds to step 1295 to end the present routine tentatively. As described above, when the main feedback condition is not satisfied, the main feedback amount DFi is set to (at) "0". Accordingly, the correction for the base fuel injection amount Fbase with the main feedback amount DFi is not performed.

<Determination of an Air-Fuel Ratio Imbalance Among Cylinders>

Next will be described processes for performing "the determination of an air-fuel ratio imbalance among cylinders". The CPU 71 is configured in such a manner that it executes "a routine for determining an air-fuel ratio imbalance among cylinders" shown by a flowchart in FIG. 13 every elapse of 4 ms (a predetermined constant sampling time ts).

Accordingly, at an appropriate timing, the CPU 71 starts process from step 1300 to proceed to step 1305 at which the CPU 71 determines whether or not a value of a flag of permission for obtaining a parameter Xkyoka is "1".

The value of the flag of permission for obtaining a parameter Xkyoka is set to (at) "1", if "a condition for obtaining a parameter for imbalance determination" is satisfied when the absolute crank angle CA coincides with 0° crank angle. The value of the flag of permission for obtaining a parameter Xkyoka is set to (at) "0" immediately after the condition for obtaining a parameter for imbalance determination is not satisfied. The condition for obtaining a parameter for imbalance determination is also simply referred to as "a condition of permission for obtaining a parameter".

The condition of permission for obtaining a parameter is satisfied when all of conditions (conditions C1 to C6) described below are satisfied. Accordingly, the condition of permission for obtaining a parameter is not satisfied when at least one of the conditions (conditions C1 to C6) is not satisfied. It should be noted that the conditions which constitute the condition of permission for obtaining a parameter are not limited to the conditions C1 to C6 described below.

(Condition C1)

The final determination of air-fuel ratio imbalance among cylinders has not been obtained yet after the current start of the engine 10. The condition C1 is also referred to as an imbalance determination execution requirement condition. The condition C1 may be replaced with a condition that either one of "an accumulated operation time of the engine 10 and an integrated value of the intake air flow rate Ga" after a previous determination of air-fuel ratio imbalance is larger than or equal to a predetermined value.

(Condition C2)

The intake air flow rate Ga obtained by the air-flow meter 61 is within a predetermined range.

(Condition C3)

The engine rotational speed NE is within a predetermined range. That is, the engine rotational speed NE is larger than or equal to a lower side engine rotational speed threshold NELoth and smaller than or equal to a higher side engine rotational speed threshold NEHith.

(Condition C4)

The engine coolant temperature THW is higher than or equal to a engine coolant temperature threshold THWth.

(Condition C5)

The main feedback condition is satisfied.

(Condition C6)

The fuel cut control is not being performed.

Here, it is assumed that the value of the flag of permission for obtaining a parameter Xkyoka is set to (at) "1", when the condition of permission for obtaining a parameter becomes satisfied under a condition that the determination of air-fuel ratio imbalance has not been performed yet after the current start of the engine 10. In this case, the CPU 71 makes a "Yes" determination at step 1305 to proceed to step 1310 at which the CPU 71 sets the value of the forced air-fuel-ratio-shift flag Xyose to (at) "1".

Figure 11:
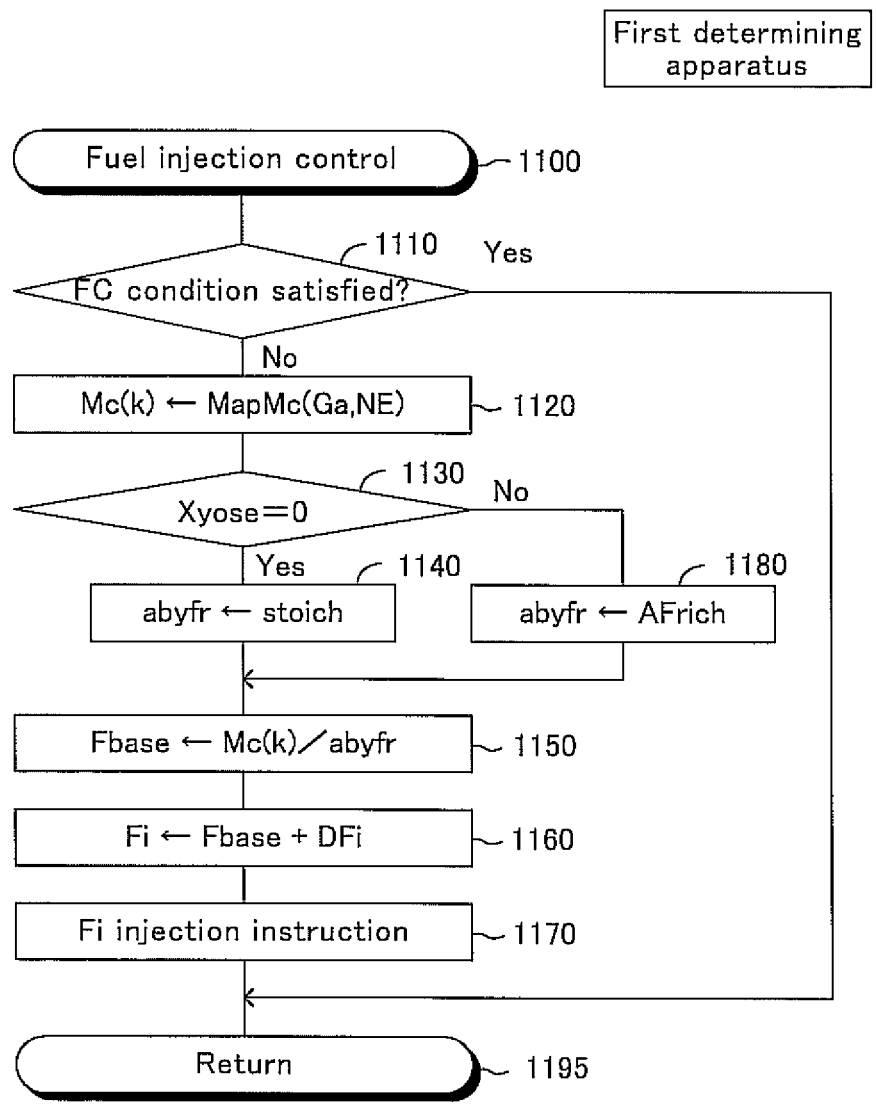
FIG. 11 is a flowchart showing a routine executed by a CPU of the air-fuel ratio imbalance among cylinders determining apparatus (first determining apparatus) according to a first embodiment of the present invention.

When the value of the forced air-fuel-ratio-shift flag Xyose flag is set to (at) "1" at step 1310 as described above, the target air-fuel ratio abyfr is set to (at) the target rich air-fuel ratio AFrich (the non-stoichiometric air-fuel ratio) at step 1180 in FIG. 11. As a result, the air-fuel ratio of the engine is controlled so that it becomes equal to the target rich air-fuel ratio AFrich. That is, the forced air-fuel-ratio-shift-control is started, and therefore, the air-fuel ratio of the engine (and accordingly, the air-fuel ratio of the exhaust gas) fluctuates (varies) in the vicinity of the target rich air-fuel ratio AFrich around the target rich air-fuel ratio AFrich.

Subsequently, the CPU 71 proceeds to step 1315 to obtain "the output value Vabyfs of the air-fuel ratio sensor 67 at that time" by an A/D conversion.

Subsequently, the CPU 71 proceeds to step 1320 to obtain a present (current) detected air-fuel ratio abyfs by applying the output value Vabyfs obtained at step 1315 to the air-fuel ratio conversion table Mapabyfs shown in FIG. 4. It should be noted that the CPU 71 stores the detected air-fuel ratio abyfs which was obtained in the previous execution of the present routine as a previous detected air-fuel ratio abyfsold, before processing the step 1320. That is, the previous detected air-fuel ratio abyfsold is the detected air-fuel ratio abyfs 4 ms (the sampling time ts) before the present time. An initial value of the previous detected air-fuel ratio abyfsold is set at a value corresponding to the stoichiometric air-fuel ratio.

Subsequently, the CPU 71 proceeds to step 1325 at which the CPU 71, (A) obtains the detected air-fuel ratio changing rate $\Delta AF$, (B) renew an integrated value SAFD of (or integrating) the absolute value $|\Delta AF|$ of the detected air-fuel ratio changing rate $\Delta AF$, and (C) renew a cumulated number counter Cn showing how many times the absolute value $|\Delta AF|$ of the detected air-fuel ratio changing rate $\Delta AF$ is accumulated (integrated) to the integrated value SAFD.

Next will be described the ways in which these values are renewed specifically.

(A) Obtainment of the detected air-fuel ratio changing rate $\Delta AF$:

The detected air-fuel ratio changing rate $\Delta AF$ is a base data (a basic indicative value) of the parameter for imbalance determination. The CPU 71 obtains the detected air-fuel ratio changing rate $\Delta AF$ by subtracting the previous detected air-fuel ratio abyfsold from the present detected air-fuel ratio abyfs. That is, when the present detected air-fuel ratio abyfs is expressed as abyfs(n) and the previous detected air-fuel ratio abyfs is expressed as abyfs(n−1), the CPU 71 obtains "the present detected air-fuel ratio abyfs $\Delta AF(n)$" at step 1325, according to a formula in (8) described below.

$$\Delta AF(n)=abyfs(n)-abyfs(n-1) \tag{8}$$

(B) Renewal of the integrated value SAFD of the absolute value $|\Delta AF|$ of the detected air-fuel ratio changing rate $\Delta AF$:

The CPU 71 obtains the present integrated value SAFD(n) according to a formula in (9) described below. That is, the CPU 71 adds the present absolute value $|\Delta AF(n)|$ of the detected air-fuel ratio changing rate $\Delta AF(n)$ obtained as described above to the previous integrated value SAFD(n−1) existing when the CPU 71 proceeds to step 1325.

$$SAFD(n)=SAFD(n-1)+|\Delta AF(n)| \tag{9}$$

The reason why "the present absolute value |ΔAF(n)| of the detected air-fuel ratio changing rate" is added to the integrated value SAFD is that the detected air-fuel ratio changing rate ΔAF(n) can become both a positive value and a negative value, as understood from (B) and (C) in FIG. 5. It should be noted that the integrated value SAFD is set to (at) "0" in the initialization routine.

(C) Renewal of the cumulated number counter Cn of the absolute value |ΔAF| of the detected air-fuel ratio changing rate ΔAF to the integrated value SAFD:

The CPU 71 increments a value of the counter Cn by "1" according to a formula in (10) described below. The Cn(n) represents the counter Cn after the renewal, and the Cn(n−1) represents the counter Cn before the renewal. The value of the counter Cn is set at "0" in the initialization routine described above, and is also set to (at) "0" at step 1370 described later. The value of the counter Cn therefore represents the number of data of the absolute value |ΔAF| of the detected air-fuel ratio changing rate ΔAF which has been accumulated in the integrated value SAFD.

$$Cn(n)=Cn(n-1)+1 \quad (10)$$

Subsequently, the CPU 71 proceeds to step 1330 to determine whether or not the crank angle CA (the absolute crank angle CA) measured with reference to a top dead center of a compression stroke of a reference cylinder (in the present example, the first cylinder) reaches 720° crank angle. When the absolute crank angle CA is less than 720° crank angle, the CPU 71 makes a "No" determination at step 1330 to directly proceed to step 1395 at which the CPU 71 ends the present routine tentatively.

It should be noted that step 1330 is a step to define the smallest unit period (the unit combustion cycle period) for obtaining a mean (or average) value of the absolute value |ΔAF| of the detected air-fuel ratio changing rate ΔAF. Here, the 720° crank angle corresponds to the smallest unit period. The smallest unit period may obviously be shorter than the 720° crank angle, however, may preferably be a time period longer than or equal to a period having an integral multiple of the sampling time ts. That is, it is preferable that the smallest unit period be determined in such a manner that a plurality of the detected air-fuel ratio changing rates ΔAFs are obtained in the smallest unit period.

Meanwhile, if the absolute crank angle CA reaches 720° crank angle when the CPU 71 executes the process of step 1330, the CPU 71 makes a "Yes" determination at step 1330 to proceed to step 1335.

The CPU 71, at step 1335:

(D) calculates a mean (average) value AveΔAF of the absolute value |ΔAF| of the detected air-fuel ratio changing rate ΔAF,
(E) renews an integrated value Save of the mean value AveΔAF, and
(F) renews a cumulated number counter Cs.

Next will be described the ways in which these values are renewed specifically.

(D) Calculation of the mean value AveΔAF of the absolute value |ΔAF| of the detected air-fuel ratio changing rate ΔAF:

The CPU 71 calculates the mean value AveΔAF (=SAFD/Cn) of the absolute value |ΔAF| of the detected air-fuel ratio changing rate ΔAF by dividing the integrated value SAFD by a value of the counter Cn. Thereafter, the CPU 71 sets the integrated value SAFD to (at) "0".

(E) Renewal of the integrated value Save of the mean value AveΔAF:

The CPU 71 obtains the present integrated value Save(n) according to a formula in (11) described below. That is, the CPU 71 renews the integrated value Save by adding the present mean value AveΔAF obtained as described above to the previous integrated value Save(n−1) existing when the CPU 71 proceeds to step 1335. A value of the integrated value Save(n) is set to (at) "0" in the initialization routine described above.

$$Save(n)=Save(n-1)+Ave\Delta AF \quad (11)$$

(F) Renewal of the cumulated number counter Cs:

The CPU 71 increments a value of the counter Cs by "1" according to a formula in (12) described below. The Cs(n) represents the counter Cs after the renewal, and the Cs(n−1) represents the counter Cs before the renewal. The value of the counter Cs is set to (at) "0" in the initialization routine described above. The value of the counter Cs therefore represents the number of data of the mean value AveΔAF which has been accumulated in the integrated value Save.

$$Cs(n)=Cs(n-1)+1 \quad (12)$$

Subsequently, the CPU 71 proceeds to step 1340 to determine whether or not the value of the counter Cs is larger than or equal to a threshold value Csth. When the value of the counter Cs is less than the threshold value Csth, the CPU 71 makes a "No" determination at step 1340 to directly proceed to step 1395 at which the CPU 71 ends the present routine tentatively. It should be noted that the threshold value Csth is a natural number, and is preferably larger than or equal to 2.

Meanwhile, if the value of the counter Cs is larger than or equal to the threshold value Csth when the CPU 71 executes the process of step 1340, the CPU 71 makes a "Yes" determination at step 1340 to proceed to step 1345 at which the CPU 71 obtains the parameter X for imbalance determination which is the air-fuel-ratio-variation-indicative-value AFD by dividing the integrated value Save by the value of the counter Cs (=Csth) according to a formula (13) described below. That is, the first determining apparatus adopts the parameter X for imbalance determination as the air-fuel-ratio-variation-indicative-value AFD (=Save/Csth). The parameter X for imbalance determination is a value obtained by averaging the mean value of the absolute value |ΔAF| of the detected air-fuel ratio changing rate ΔAF for each of the unit combustion cycle periods, for a plurality (Cs) of unit combustion cycle periods.

$$X=Save/Csth \quad (13)$$

Subsequently, the CPU 71 proceeds to step 1350 to determine whether or not the parameter X for imbalance determination is larger than "the threshold value Xth for imbalance determination". The threshold value Xth for imbalance determination in this case is equal to a threshold value XHith shown by a line L2 in FIG. 6, for example. That is, the threshold value Xth for imbalance determination is set such that the air-fuel ratio imbalance (state) among cylinders is occurring without any question if the parameter X for imbalance determination which is obtained in the rich region (or the lean region) is larger than the threshold value Xth for imbalance determination, and the air-fuel ratio imbalance (state) among cylinders is not occurring without any question if the parameter X for imbalance determination is smaller than the threshold value Xth for imbalance determination.

The parameter X for imbalance determination is obtained while the forced air-fuel-ratio-shift-control is being carried out. Accordingly, it is possible to determine that the air-fuel ratio imbalance (state) among cylinders is occurring when the parameter X for imbalance determination is larger than the threshold value Xth for imbalance determination, and it is possible to determine that the air-fuel ratio imbalance (state) among cylinders is not occurring when the parameter X for imbalance determination is smaller than the threshold value Xth for imbalance determination, since the responsivity of the air-fuel ratio sensor 67 is sufficiently high.

Accordingly, if the parameter X for imbalance determination is larger than the threshold value Xth for imbalance determination, the CPU 71 makes a "Yes" determination at step 1350 to proceed to step 1355 at which it sets a value of an imbalance occurrence flag XINB to (at) "1". That is, the CPU 71 determines that the air-fuel ratio imbalance (state) among cylinders is occurring. Further, at this time, the CPU 71 may turn on a warning light which is not shown. It should be noted that the value of the imbalance occurrence flag XINB is stored in the Backup RAM 74.

Subsequently, the CPU 71 proceeds to step 1365 to set the forced air-fuel-ratio-shift flag Xyose to (at) "0". As a result, the target air-fuel ratio abyfr is returned to the stoichiometric air-fuel ratio stoich, and the forced air-fuel-ratio-shift control is therefore ended (terminated). That is, the normal air-fuel ratio feedback control is resumed to have the air-fuel ratio of the engine coincide with the stoichiometric air-fuel ratio.

To the contrary, if the parameter X for imbalance determination is smaller than the threshold value Xth for imbalance determination when the CPU 71 executes the process of step 1350, the CPU 71 makes a "No" determination at step 1350 to proceed to step 1360 to set the value of the imbalance occurrence flag XINB to (at) "2". That is, the CPU 71 stores the fact that "a determination that the air-fuel ratio imbalance (state) among cylinders is not occurring is made as a result of the determination of an air-fuel ratio imbalance among cylinders". Thereafter, the CPU 71 proceeds to step 1365 and step 1395 to end the present routine tentatively. As described above, the determination of an air-fuel ratio imbalance among cylinders is carried out.

It should be noted that, if the value of the flag of permission for obtaining a parameter Xkyoka is not "1" when the CPU 71 proceeds to step 1305, the CPU 71 makes a "No" determination to proceed to step 1370. Thereafter, the CPU sets (or clears) each of the values (e.g., $\Delta AF$, SAFD, Cn, and so on) to (at) "0" at step 1370. Subsequently, the CPU 71 proceeds to step 1375 to set the value of the forced air-fuel-ratio-shift flag Xyose to (at) "0", and thereafter, directly proceeds to step 1395 to end the present routine tentatively. That is, when the condition for obtaining a parameter for imbalance determination is not satisfied, the value of the forced air-fuel-ratio-shift flag Xyose is set to (at) "0", and the forced air-fuel-ratio-shift control is therefore not performed, so that the air-fuel ratio of the engine is controlled so as to coincide with the stoichiometric air-fuel ratio.

As described above, the first determining apparatus is applied to the engine 10 having a plurality of cylinders.

Further, the first determining apparatus comprises the air-fuel ratio sensor 67, a plurality of the injectors 39, and instructed fuel injection amount control means for controlling the instructed fuel injection amount Fi in such a manner that the air-fuel ratio of the mixture supplied to the combustion chambers 25 of the two or more of the cylinders (in the present example, all of the cylinders) discharging the exhaust gas which reaches the air-fuel ratio sensor 67 coincides with (becomes equal to) the target air-fuel ratio abyfr (the routines of FIGS. 11 and 12).

Figure 13:
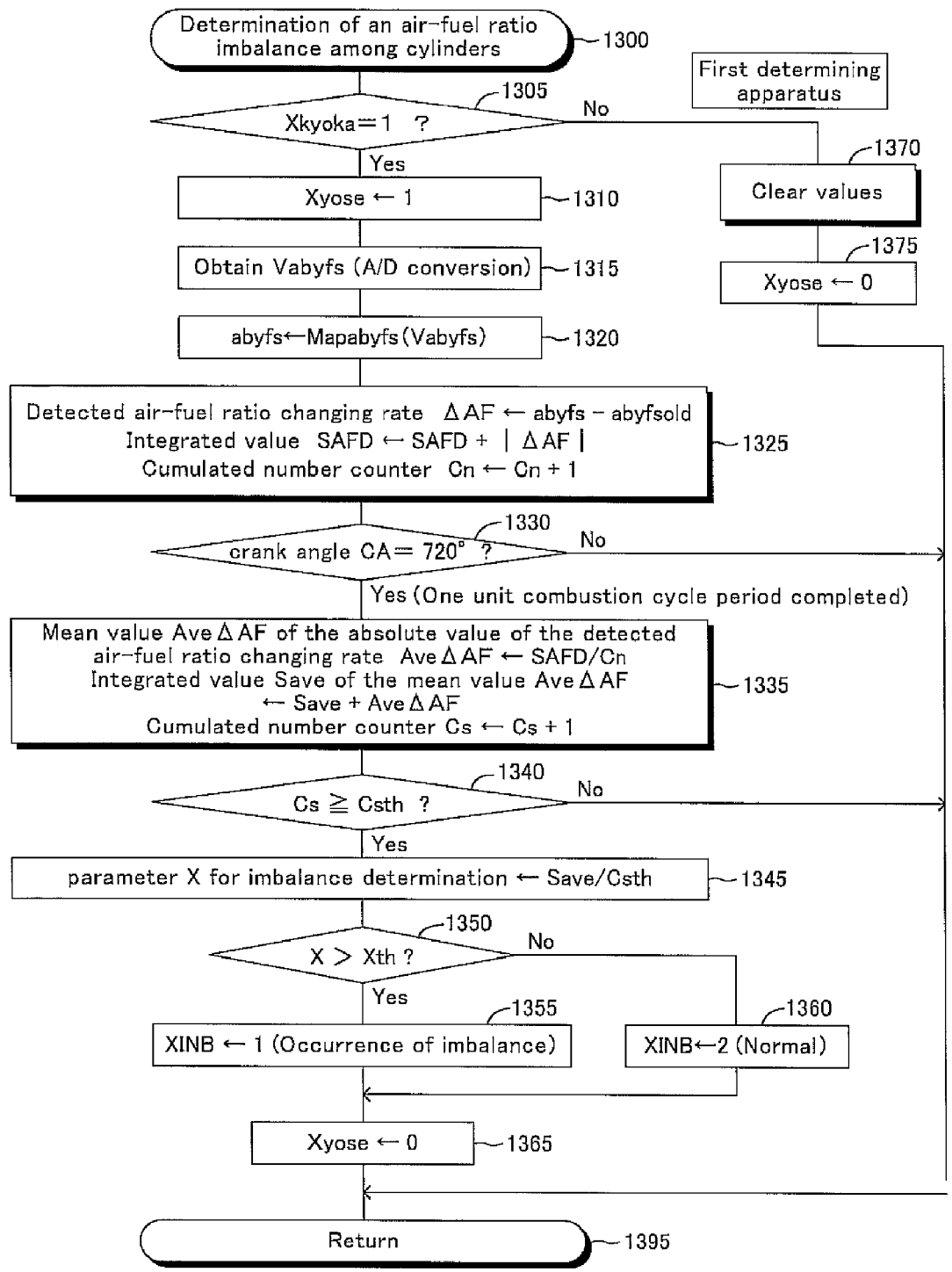
FIG. 13 is a flowchart showing a routine executed by the CPU of the first determining apparatus.

Furthermore, the first determining apparatus comprises the imbalance determining means which, obtains the parameter X for imbalance determination which becomes larger (or increases) as the variation (or the fluctuation) of the air-fuel ratio of the exhaust gas passing through the position at which the air-fuel ratio sensor 67 is disposed becomes larger, based on "the output value Vabyfs of the air-fuel ratio sensor 67";

determines that "the air-fuel ratio imbalance (state) among cylinders" is occurring when the obtained parameter X for imbalance determination is larger than the predetermined threshold value Xth for imbalance determination, and determines that "the air-fuel ratio imbalance (state) among cylinders is not occurring" when the obtained parameter X for imbalance determination is smaller than the predetermined threshold value Xth for imbalance determination (the routine of FIG. 13).

In addition, the imbalance determining means of the first determining apparatus, in a period in which the predetermined condition for obtaining a parameter for imbalance determination is satisfied, sets the target air-fuel ratio abyfr to (at) "the non-stoichiometric air-fuel ratio (the target rich air-fuel ratio AFrich or the target lean air-fuel ratio AFlean) which is the air-fuel ratio other than the stoichiometric air-fuel ratio" (step 1310 of FIG. 13, step 1130 and step 1180 of FIG. 11), and obtains the parameter X for imbalance determination (from step 1315 to step 1345 of FIG. 13).

Further, the imbalance determining means is configured in such a manner that it sets the target air-fuel ratio abyfr to (at) the stoichiometric air-fuel ratio stoich in a period in which the predetermined condition for obtaining a parameter for imbalance determination is not satisfied (step 1365 and step 1375 of FIG. 13, the unillustrated initialization routine, step 1130 and 1140 of FIG. 11).

According to the above described configuration, the parameter X for imbalance determination is obtained, when "the air-fuel ratio of the exhaust gas of the engine varies in the vicinity of (near or around) the non-stoichiometric air-fuel ratio (during the forced air-fuel-ratio-shift-control is being performed)" owing to the setting the target air-fuel ratio to (at) the non-stoichiometric air-fuel ratio. That is, the parameter X for imbalance determination is obtained based on the output value Vabyfs of the air-fuel ratio sensor 67, "when the output value Vabyfs of the air-fuel ratio sensor 67 can vary depending on (or follow) the variation (fluctuation) of the air-fuel ratio of the exhaust gas without a long delay".

Therefore, according to the first determining apparatus, it is possible to determine whether or not the air-fuel ratio imbalance state among cylinders is occurring with great certainty, since the parameter X for imbalance determination can become a value which represents the degree of the air-fuel ratio imbalance state among cylinders (i.e., the difference between individual cylinder air-fuel-ratios) with great accuracy. It should be noted that the CPU 71 may set the target air-fuel ratio abyfr to (at) an air-fuel ratio other the stoichiometric air-fuel ratio when a particular condition is satisfied at step 1140 of FIG. 11, and may set the target air-fuel ratio abyfr to (at) the stoichiometric air-fuel ratio when the particular condition is not satisfied at step 1140 of FIG. 11.

Second Embodiment

Next will be described a determining apparatus (hereinafter simply referred to as "a second determining apparatus") according to a second embodiment of the present invention.

The second determining apparatus firstly sets the target air-fuel ratio abyfr to (at) the stoichiometric air-fuel ratio stoich. More specifically, the second determining apparatus sets the target air-fuel ratio abyfr to (at) the stoichiometric air-fuel ratio stoich when the condition for obtaining a parameter for imbalance determination is not satisfied, except for a particular case such as an after-engine-start-condition.

The second determining apparatus obtains the parameter X for imbalance determination (the air-fuel-ratio-variation-indicative-value AFD) while the apparatus maintains the target air-fuel ratio abyfr at the stoichiometric air-fuel ratio stoich, when the condition for obtaining a parameter for imbalance determination is satisfied, according to a manner similar to a manner of the first determining apparatus. The parameter X for imbalance determination which is obtained while the target air-fuel ratio abyfr is maintained at the stoichiometric air-fuel ratio stoich is referred to as "a tentative parameter X", for convenience.

After the tentative parameter X is obtained, the second determining apparatus compares the tentative parameter X with the predetermined threshold value XHith (refer to the line L2 in FIG. 6) for imbalance determination, and determines that the air-fuel ratio imbalance (state) among cylinders is occurring when the tentative parameter X is larger than the threshold value XHith for imbalance determination.

The threshold value XHith for imbalance determination is set to (at) a relatively large value such that, if the tentative parameter X which is obtained when the responsivity of the air-fuel ratio sensor 67 is relatively low is larger than the threshold value XHith for imbalance determination, the difference between individual cylinder air-fuel-ratios must be sufficiently large, and thus, it is possible to clearly (without doubt) determine that the air-fuel ratio imbalance (state) among cylinders is occurring. Accordingly, the threshold value XHith for imbalance determination is also referred to as a high side threshold value XHith.

Figure 6:
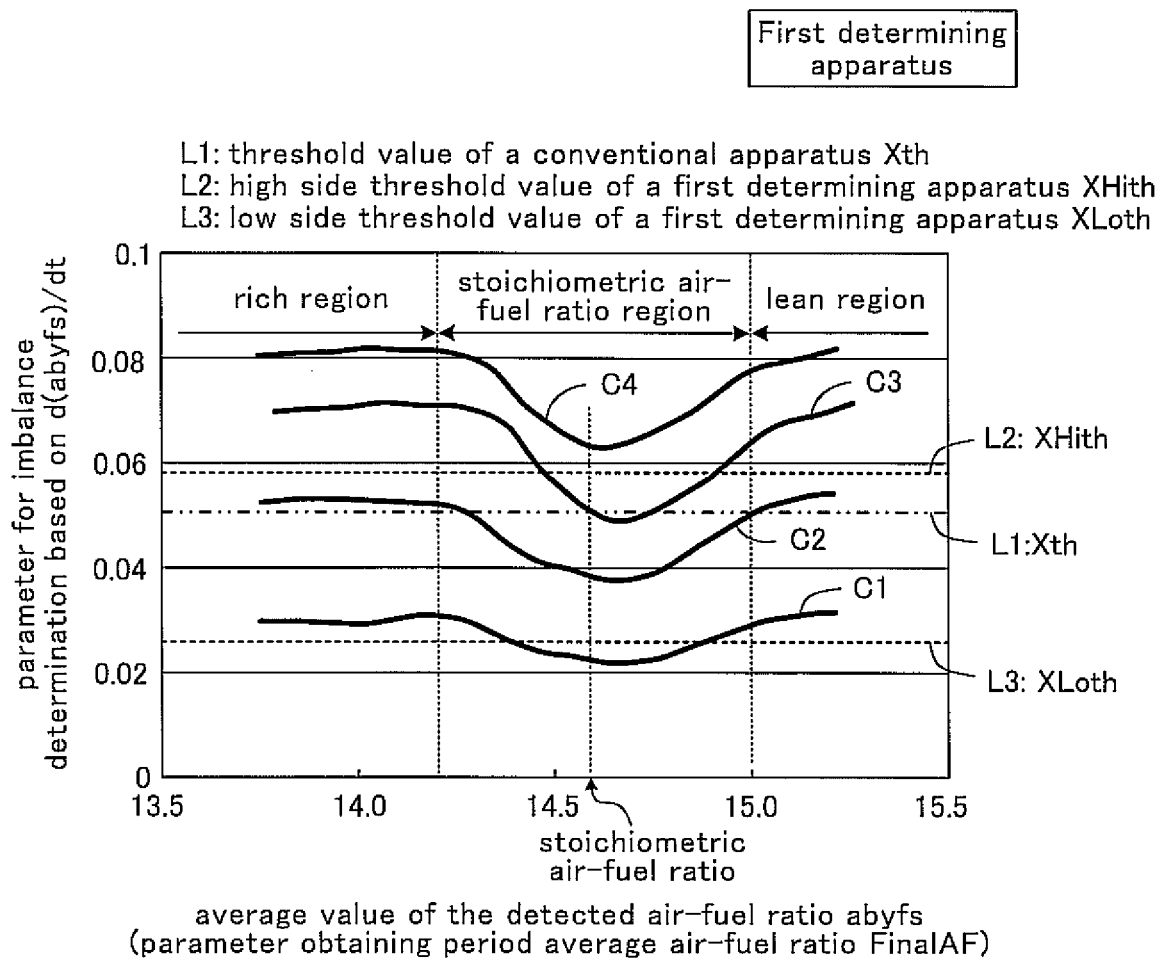
FIG. 6 is a graph showing a relationship between a parameter obtaining period average air-fuel ratio and the parameter for imbalance determination.

On the other hand, when the tentative parameter X is smaller than the high side threshold value XHith, the second determining apparatus compares the tentative parameter X with a low side threshold value XLoth (refer to a line L3 in FIG. 6). The low side threshold value XLoth is smaller than the high-side threshold value XHith by a predetermined value. The low side threshold value XLoth is set to (at) a relatively small value such that it is possible to clearly (without doubt) determine that "the air-fuel ratio imbalance (state) among cylinders is not occurring", if the tentative parameter X is smaller than the low side threshold value XLoth. The second determining apparatus determines that the air-fuel ratio imbalance (state) among cylinders is not occurring, when the tentative parameter X is smaller than the low side threshold value XLoth. Thereafter, the second determining apparatus does not perform "the forced air-fuel-ratio-shift-control in which the target air-fuel ratio is set to (at) the non-stoichiometric air-fuel ratio" until the operation of the engine 10 is stopped, and ends the imbalance determination.

Meanwhile, the second determining apparatus defers or suspends the determination as to whether or not the air-fuel ratio imbalance (state) among cylinders is occurring, when "the tentative parameter X is smaller than the high side threshold value XHith and is larger than the low side threshold value XLoth", and sets the target air-fuel ratio abyfr to (at) the non-stoichiometric air-fuel ratio (the target rich air-fuel ratio AFrich or the target lean air-fuel ratio AFlean). As described before, the non-stoichiometric air-fuel ratio is set at the air-fuel ratio (e.g., 14.2 or less, or, 15 or more) which causes the responsivity of the air-fuel ratio sensor 67 to become sufficiently high with respect to the variation of the air-fuel ratio of the exhaust gas.

The second determining apparatus again obtains the parameter X for imbalance determination according to the manner described above, with maintaining the target air-fuel ratio abyfr at the non-stoichiometric air-fuel ratio. The parameter X for imbalance determination which is obtained while the target air-fuel ratio abyfr is maintained at the non-stoichiometric air-fuel ratio is referred to as "a final parameter X", for convenience.

After the final parameter X is obtained, the second determining apparatus compares the final parameter X with the threshold value Xth for imbalance determination (the threshold value Xth for imbalance determination is equal to the high-side threshold value XHith, in the second determining apparatus), and determines that the air-fuel ratio imbalance (state) among cylinders is occurring when the final parameter X is larger than the threshold value Xth for imbalance determination. To the contrary, the second determining apparatus determines that the air-fuel ratio imbalance (state) among cylinders is not occurring when the final parameter X is smaller than the threshold value Xth for imbalance determination. This is the principle that the second determining apparatus adopts for determination of an air-fuel ratio imbalance among cylinders. It should be noted that the threshold value Xth for imbalance determination may be set at an appropriate value between the high side threshold value XHith and the low side threshold value XLoth. In other words, the high side threshold value XHith is larger than or equal to the threshold value Xth for imbalance determination, and the low side threshold value XLoth is smaller than the threshold value Xth for imbalance determination.

(Actual Operation)

The CPU 71 of the second determining apparatus executes routines shown in FIGS. 11 and 12, similarly to the CPU 71 of the first determining apparatus. Further, the CPU 71 of the second determining apparatus executes a routine shown by flowcharts in "FIGS. 14 to 16" instead of the routine shown in FIG. 13. The routines shown in FIGS. 11 and 12 have been already described. Accordingly, the routines shown in FIGS. 14 to 16 will be described hereinafter. It should be noted that each step in FIGS. 14 to 16 at which the same processing is performed as each step shown in FIG. 13 is given the same numeral as one given to such step shown in FIG. 13.

Now, it is assumed here that the value of the flag of permission for obtaining parameter Xkyoka is set to (at) "1", when the condition of permission for obtaining a parameter becomes satisfied under a condition that the imbalance determination has not been made yet after the start of the engine 10. In this case, the CPU 71 makes a "Yes" determination at step 1305 in FIG. 14 to proceed to step 1410 at which the CPU 71 determines whether or not a value of a forced air-fuel-ratio-shift requesting flag Xyosereq is "1".

The value of the forced air-fuel-ratio-shift requesting flag Xyosereq is set to (at) "0" in the initialization routine described above, and set to (at) "1" after the tentative parameter X is obtained and after the imbalance determination is made based on the tentative parameter X (and further, the imbalance determination is suspended) (refer to step 1580 of FIG. 15 described later).

Accordingly, the value of the forced air-fuel-ratio-shift requesting flag Xyosereq is "0" at the present time. This causes the CPU 71 to make a "No" determination at step 1410 to proceed to step 1420 at which the CPU 71 sets the value of the forced air-fuel-ratio-shift flag Xyose to (at) "0". As a result, the target air-fuel ratio abyfr is maintained at the stoichiometric air-fuel ratio stoich. It should be noted that the value of the forced air-fuel-ratio-shift flag Xyose is set to (at) "0" in the initialization routine. Accordingly, the process of step 1420 does not substantially change the value of the forced air-fuel-ratio-shift flag Xyose.

Thereafter, the CPU 71 obtains the parameter X for imbalance determination as "the tentative parameter X" based on the processes of the steps from 1315 to 1345. That is, the parameter X for imbalance determination is obtained while the normal air-fuel ratio feedback control is being performed in order to have the air-fuel ratio of the engine coincide with the stoichiometric air-fuel ratio, and the parameter X for imbalance determination is adopted as the tentative parameter X.

After the tentative parameter X is obtained at step 1345, the CPU 71 proceeds to step 1440 to set a value of a parameter obtainment completion flag Xobtain to (at) "1". The parameter obtainment completion flag Xobtain is also set to (at) "0" in the initialization routine described above. Subsequently, the CPU 71 proceeds to step 1495 to end the present routine tentatively.

Figure 15:
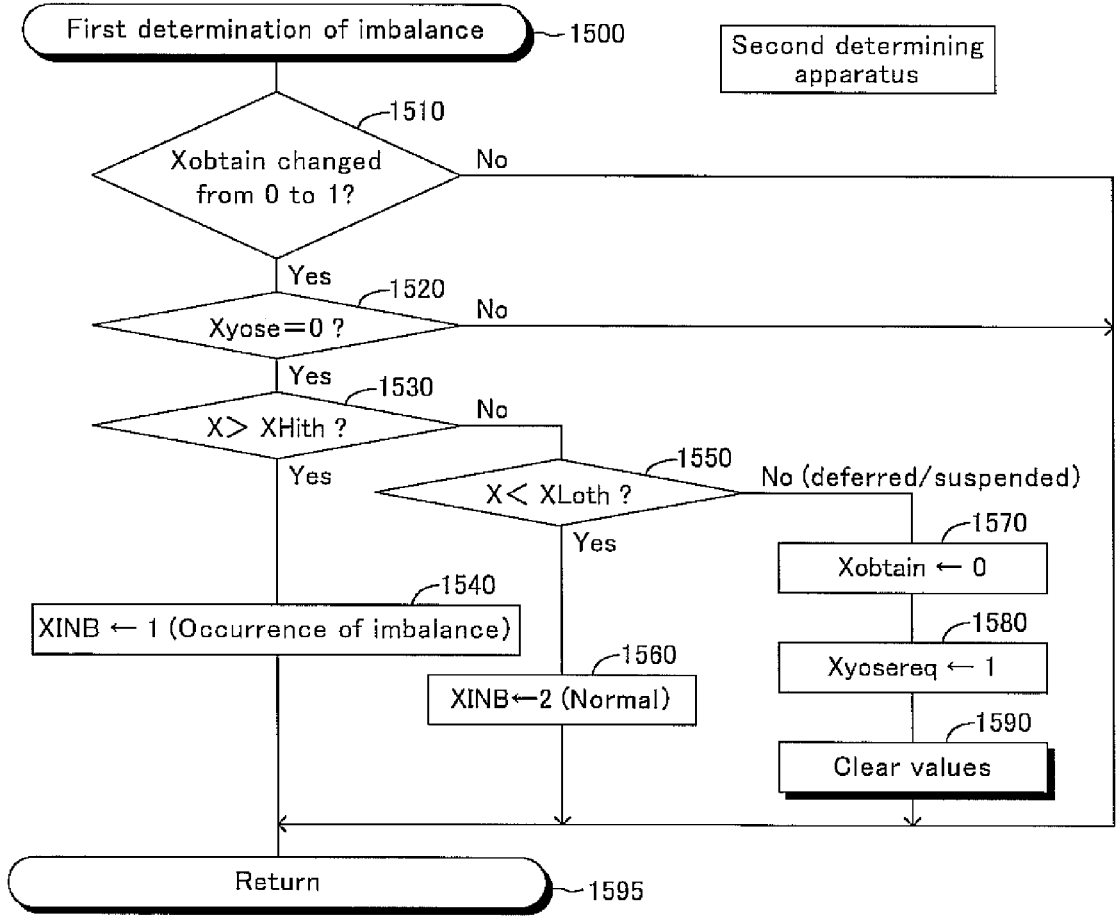
FIG. 15 is a flowchart showing a routine executed by the CPU of the second determining apparatus.

Meanwhile, the CPU 71 starts the routine of FIG. 15 from step 1500 at a certain timing, and determines "whether or not the present time is immediately after a timing at which the value of the parameter obtainment completion flag Xobtain is changed from "0" to "1", at step 1510. The CPU 71 makes a "No" determination at step 1510 when the determining condition in step 1510 is not satisfied, and then directly proceeds to step 1595 to end the present routine tentatively.

Figure 16:
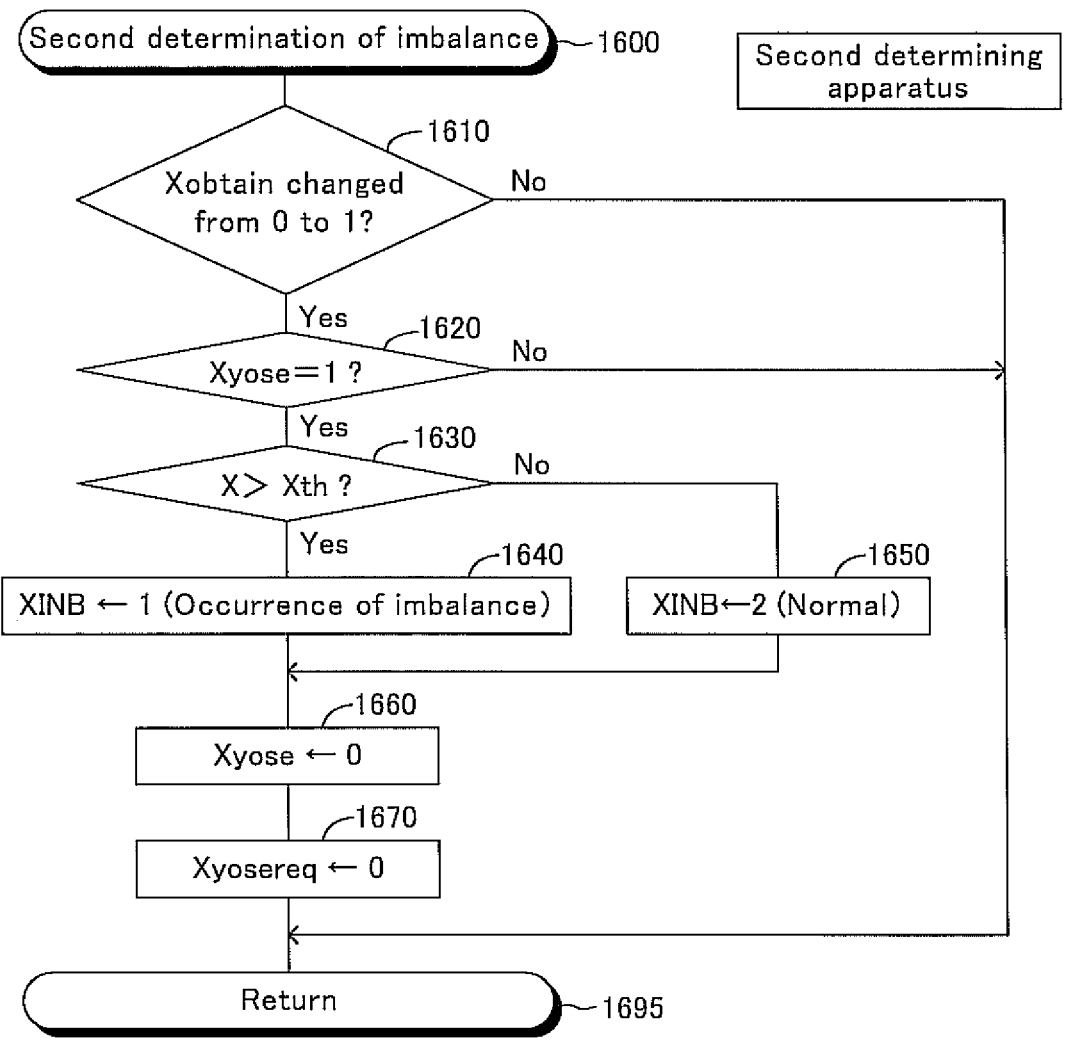
FIG. 16 is a flowchart showing a routine executed by the CPU of the second determining apparatus.

Similarly, the CPU 71 starts the routine of FIG. 16 from step 1600 at a certain timing, and determines "whether or not the present time is immediately after a timing at which the value of the parameter obtainment completion flag Xobtain is changed from "0" to "1", at step 1610. The CPU 71 makes a "No" determination at step 1610 when the determining condition in step 1610 is not satisfied, and then directly proceeds to step 1695 to end the present routine tentatively.

Figure 14:
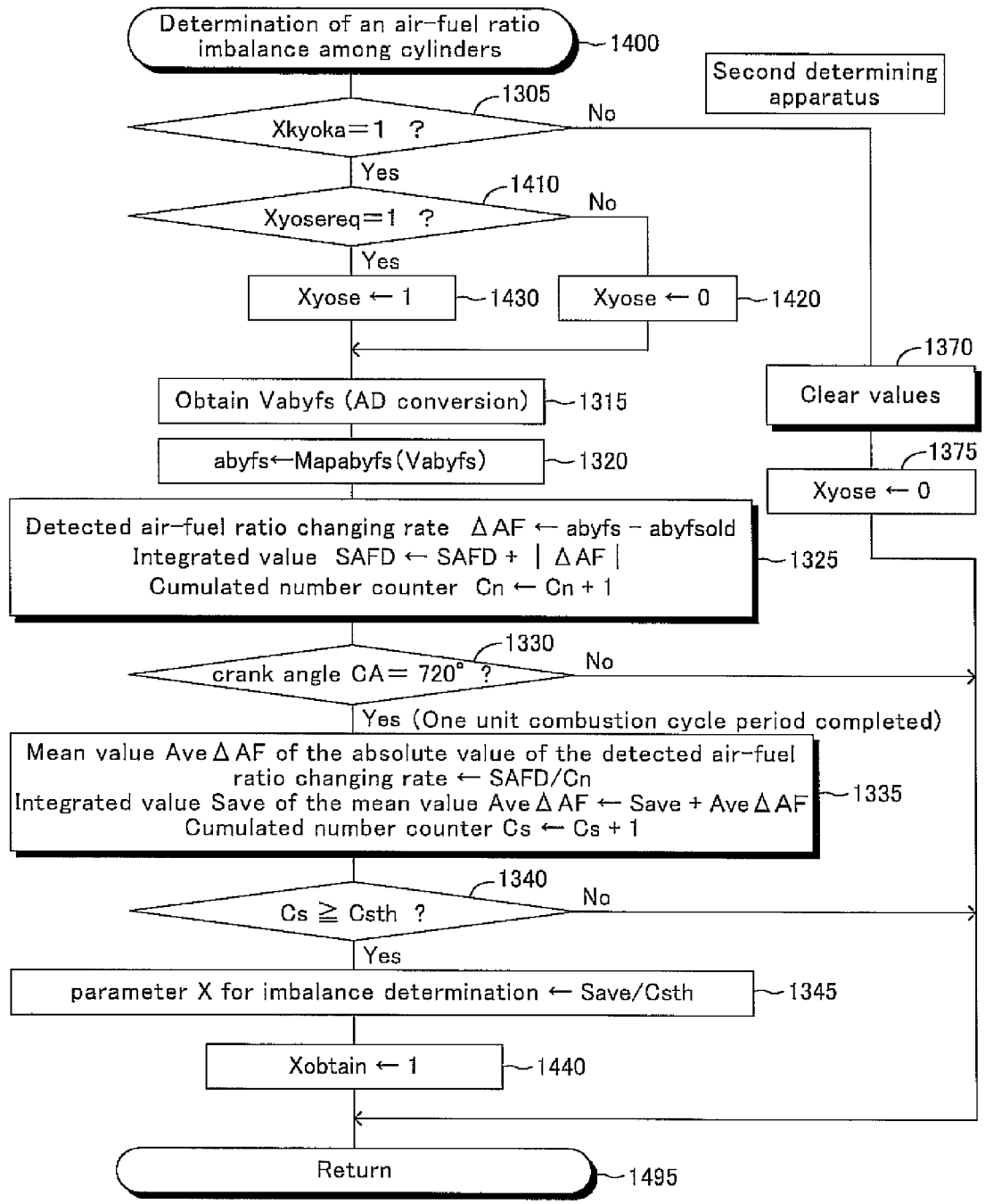
FIG. 14 is a flowchart showing a routine executed by a CPU of an air-fuel ratio imbalance among cylinders determining apparatus (second determining apparatus) according to a second embodiment of the present invention.

Accordingly, after the value of the parameter obtainment completion flag Xobtain is changed to "1" by the process of the step 1440 in FIG. 14, the CPU 71 makes a "Yes" determination at step 1510 when the CPU 71 proceeds to step 1510, and thus, the CPU 71 proceeds to step 1520 to determine whether or not the value of the forced air-fuel-ratio-shift flag Xyose is "0".

At the present time, the value of the forced air-fuel-ratio-shift flag Xyose is "0". The CPU 71 therefore makes a "Yes" determination at step 1520 to proceed to step 1530 at which the CPU 71 determines whether or not the value of the tentative parameter X is larger than "the high side threshold value XHith shown by the line L2 in FIG. 6".

At the present time, if the tentative parameter X is larger than the high side threshold value XHith, the CPU 71 makes a "Yes" determination at step 1530 to proceed to step 1540 at which the CPU 71 sets the value of the imbalance occurrence flag XINB to (at) "1". That is, the CPU 71 determines that the air-fuel ratio imbalance (state) among cylinders is occurring. Further, at this time, the CPU 71 may turn on the warning light which is not shown. Thereafter, the CPU 71 proceeds to step 1595 to end the present routine tentatively.

To the contrary, if the tentative parameter X is smaller than the high side threshold value XHith when the CPU 71 executes the processing of the step 1530, the CPU 71 makes a "No" determination at step 1530 to proceed to step 1550 at which the CPU 71 determines whether or not the tentative parameter X is smaller than "the low side threshold value XLoth shown by the line 3 in FIG. 6".

At this time, if the tentative parameter X is smaller than the low side threshold value XLoth, then the CPU 71 makes a "Yes" determination to proceed to step 1560 at which the CPU 71 sets the imbalance occurrence flag XINB to (at) "2". That is, the CPU 71 stores the fact that "a determination that the air-fuel ratio imbalance (state) among cylinders is not occurring is made as a result of the determination of an air-fuel ratio imbalance among cylinders". Thereafter, the CPU 71 proceeds to step 1595 to end the present routine tentatively.

On the other hand, if the tentative parameter X is larger than or equal to the low side threshold value XLoth when the CPU 71 executes the process of the step 1550, the CPU 71 suspends the imbalance determination. That is, the CPU 71 suspends forming a conclusion regarding the determination as to whether or not the air-fuel ratio imbalance (state) among cylinders is occurring. Thereafter, the CPU 71 starts the forced air-fuel-ratio-shift control, and obtains the parameter X for imbalance determination again to perform the imbalance determination.

More specifically, if the tentative parameter X is larger than or equal to the low side threshold value XLoth, then the CPU 71 makes a "No" determination at step 1550 to proceed to step 1570 to set the value of the parameter obtainment completion flag Xobtain to (at) "0". Subsequently, the CPU 71 proceeds to step 1580 to set the value of the forced air-fuel-ratio-shift requesting flag Xyosereq to (at) "1". Thereafter, the CPU 71 proceeds to step 1590 to set (or clear) each of the values (e.g., ΔAF, SAFD, Cn, AveΔAF, Save, Cs and so on) used when the parameter X for imbalance determination is obtained to (at) "0", and then directly proceeds to step 1595 to end the present routine tentatively.

After this happens, when the CPU 71 again starts the processes of the routine in FIG. 14 and proceeds to step 1410, the CPU 71 makes a "Yes" determination to proceed to step 1430 at which the CPU 71 sets the value of the forced air-fuel-ratio-shift flag Xyose to (at) "1", since the value of the air-fuel-ratio-shift requesting flag Xyosereq is "1".

When the value of the forced air-fuel-ratio-shift flag Xyose is set at "1" at step 1430 as described above, the target air-fuel ratio abyfr is set to (at) the target rich air-fuel ratio AFrich (the non-stoichiometric air-fuel ratio) at step 1180 of FIG. 11. As a result, the air-fuel ratio of the engine is controlled so as to become equal to the target rich air-fuel ratio AFrich. That is, the forced air-fuel-ratio-shift control is started, and the air-fuel ratio of the engine fluctuate (varies) in the vicinity of (or around) the target rich air-fuel ratio AFrich.

Further, the CPU 71 executes the processes from step 1315 to step 1340. Accordingly, when the counter Cs becomes larger than or equal to the threshold value Csth, the CPU 71 proceeds from step 1340 to step 1345 to again obtain the parameter X for imbalance determination. This parameter X for imbalance determination is a parameter which is obtained when the target air-fuel ratio abyfr is maintained at "the non-stoichiometric air-fuel ratio which is the air-fuel ratio (i.e., the target rich air-fuel ratio AFrich) other than the stoichiometric air-fuel ratio" in a period in which the condition of permission for obtaining a parameter is satisfied. That is, the parameter X for imbalance determination is the "final parameter X". Subsequently, the CPU 71 sets the value of the parameter obtainment completion flag Xobtain to (at) "1" at step 1440 and proceeds to step 1495 to end the present routine tentatively.

As a result, the value of the parameter obtainment completion flag Xobtain is changed from "0" to "1". Accordingly, when the CPU 71 proceeds to step 1510 in FIG. 15, the CPU 71 makes a "Yes" determination to proceed to step 1520. At this time, the value of the forced air-fuel-ratio-shift flag Xyose is "1". Accordingly, the CPU 71 makes a "No" determination to directly proceed to step 1595 to end the present routine tentatively.

Meanwhile, when the CPU 71 proceeds to step 1610 in FIG. 16, the CPU 71 makes a "Yes" determination at step 1610 to proceed to step 1620. The CPU 71 determines whether or not the value of the forced air-fuel-ratio-shift flag Xyose is "1" at step 1620. At this time, the value of the forced air-fuel-ratio-shift flag Xyose is "1". Accordingly, the CPU 71 makes a "Yes" determination at step 1620 to proceed to step 1630 to determine whether or not the final parameter X is larger than the threshold value Xth for imbalance determination (which is equal to the high side threshold value XHith, in the present example).

In this case, if the final parameter X is larger than the threshold value Xth for imbalance determination, the CPU 71 makes a "Yes" determination at step 1630 to proceed to step 1640 at which it sets the value of the imbalance occurrence flag XINB to (at) "1". That is, the CPU 71 determines that the air-fuel ratio imbalance (state) among cylinders is occurring. Thereafter, the CPU 71 proceeds to step 1660.

To the contrary, if the final parameter X is smaller than or equal to the threshold value Xth for imbalance determination when the CPU 71 executes the process of step 1630, the CPU 71 makes a "No" determination at step 1630 to proceed to step 1650 to set the value of the imbalance occurrence flag XINB to (at) "2". That is, the CPU 71 stores the fact that "the determination that the air-fuel ratio imbalance (state) among cylinders is not occurring is made as a result of the determination of an air-fuel ratio imbalance among cylinders". Thereafter, the CPU 71 proceeds to step 1660.

The CPU 71 sets the value of the forced air-fuel-ratio-shift flag Xyose to (at) "0" at step 1660, and sets the value of the forced air-fuel-ratio-shift requesting flag Xyosereq to (at) "0" at step 1670, and then proceeds to step 1695 to end the present routine tentatively. As a result, the target air-fuel ratio abyfr is returned to the stoichiometric air-fuel ratio stoich, and therefore, the forced air-fuel-ratio-shift-control is terminated (ended). That is, the normal air-fuel ratio feedback control is resumed to have the air-fuel ratio of the engine coincide with the stoichiometric air-fuel ratio.

It should be noted that, if the value of the forced air-fuel-ratio-shift flag Xyose is "0" when the CPU 71 proceeds to the step 1620 in FIG. 16, then the CPU 71 makes a "No" determination to directly proceed to step 1695 to end the present routine tentatively.

As described above, the second determining apparatus comprises imbalance determining means, which maintains the target air-fuel ratio abyfr at the stoichiometric air-fuel ratio stoich and obtains the parameter X for imbalance determination as the tentative parameter X based on the output value of the air-fuel ratio sensor 67 before it sets the target air-fuel ratio abyfr at the non-stoichiometric air-fuel ratio in the period in which the predetermined condition for obtaining a parameter for imbalance determination is satisfied (the routine of FIG. 14, especially, step 1410 and step 1420).

Further, the imbalance determining means, determines that the air-fuel ratio imbalance (state) among cylinders is occurring, when the obtained tentative parameter X is larger than "the high side threshold value XHith" (step 1530 and step 1540 of FIG. 15), determines that the air-fuel ratio imbalance (state) among cylinders is not occurring, when the obtained tentative parameter X is smaller than "the low side threshold value XLoth which is smaller than the high side threshold value XHith by the predetermined value (amount)" (step 1550 and step 1560 of FIG. 15), and defers (suspends) making the determination as to whether or not the air-fuel ratio imbalance (state) among cylinders is occurring when the obtained tentative parameter X is smaller than the high side threshold value XHith and larger than the low side threshold value XLoth (refer to the "No" determination at step 1550 of FIG. 15), In addition, when the determination as to whether or not the air-fuel ratio imbalance state among cylinders is occurring is deferred or suspended, the imbalance determining means sets the target air-fuel ratio abyfr to (at) the non-stoichiometric air-fuel ratio (the target rich air-fuel ratio AFrich or the target lean air-fuel ratio AFlean) and obtains the parameter X for imbalance determination based on the output value Vabyfs of the air-fuel ratio sensor 67 as the final parameter X (refer to step 1580 of FIG. 15, step 1410, step 1430, and step 1315 to step 1345 of FIG. 14). The imbalance determining means determines that the air-fuel ratio imbalance (state) among cylinders is occurring when the obtained final parameter X is larger than "the threshold value Xth for imbalance determination" (step 1630 and step 1640 of FIG. 16), and determines that the air-fuel ratio imbalance (state) among cylinders is not occurring when the obtained final parameter X is smaller than the threshold value Xth for imbalance determination (step 1630 and step 1650 of FIG. 16).

According to the second determining apparatus, it is not necessary to set the target air-fuel ratio abyfr to (at) the non-stoichiometric air-fuel ratio in a case in which it is clearly possible to obtain a result of the imbalance determination, based on the parameter X for imbalance determination (the tentative parameter X) which is obtained while the target air-fuel ratio abyfr is maintained at the stoichiometric air-fuel ratio. Accordingly, it is possible to perform the determination of an air-fuel ratio imbalance among cylinders with keeping the emission at a low level.

Furthermore, in a case in which it is not possible to clearly determine whether or not the air-fuel ratio imbalance (state) among cylinders is occurring based on the tentative parameter X, the parameter X for imbalance determination (the final parameter X) is obtained while the target air-fuel ratio abyfr is set at the non-stoichiometric air-fuel ratio, and the imbalance determination is made based on the final parameter X. Accordingly, a false imbalance determination can be avoided.

Third Embodiment

Next will be described a determining apparatus (hereinafter simply referred to as "a third determining apparatus") according to a third embodiment of the present invention.

The third determining apparatus obtains the tentative parameter and the final parameter, similarly to the second determining apparatus. Hereinafter, in order to clearly differentiate between the tentative parameter and the final parameter, the tentative parameter X is expressed as Xz and the final parameter is expressed as Xs.

The third determining apparatus obtains a difference $\Delta X$ between the tentative parameter Xz and the final parameter Xs, and determines that the air-fuel ratio imbalance (state) among cylinders is occurring when an absolute value $|\Delta X|$ of the difference $\Delta X$ is larger than the threshold value $\Delta X$th. To the contrary, the third determining apparatus determines that the air-fuel ratio imbalance (state) among cylinders is not occurring when the absolute value $|\Delta X|$ of the difference $\Delta X$ is smaller than the threshold value $\Delta X$th.

Figure 17:
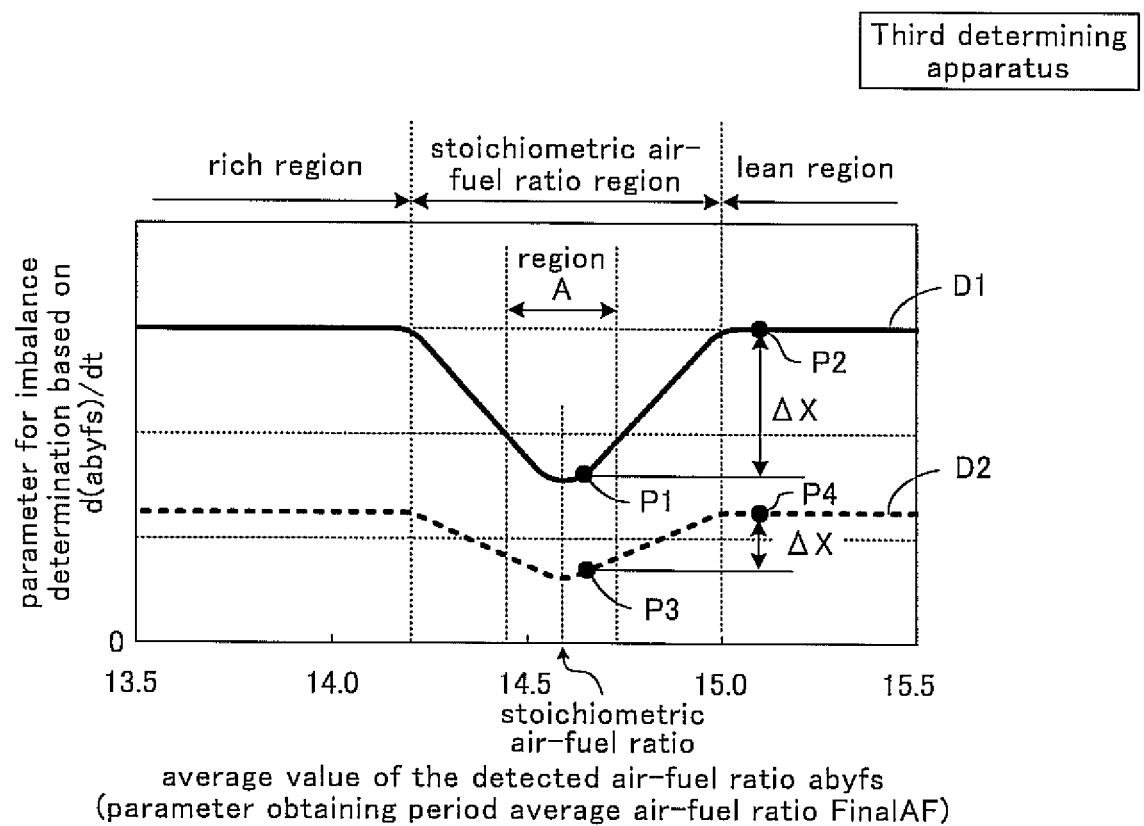
FIG. 17 is a graph for describing a principle of a determination of air-fuel ratio imbalance adopted by an air-fuel ratio imbalance among cylinders determining apparatus (third determining apparatus) according to a third embodiment of the present invention.

As shown by a solid line D1 in FIG. 17, when the air-fuel ratio imbalance (state) among cylinders is occurring, the absolute value $|\Delta X|$ of the difference $\Delta X$ between the tentative parameter Xz (refer to point P1) and the final parameter Xs (refer to point P2) becomes relatively large. On the other hand, as shown by a dotted line D2 in FIG. 17, when the air-fuel ratio imbalance (state) among cylinders is not occurring, the absolute value $|\Delta X|$ of the difference $\Delta X$ between the tentative parameter Xz (refer to point P3) and the final parameter Xs (refer to point P4) becomes relatively small.

Accordingly, the third determining apparatus determines that the air-fuel ratio imbalance (state) among cylinders is occurring when the absolute value |ΔX| of the difference ΔX is larger than the threshold value ΔXth, and determines that the air-fuel ratio imbalance (state) among cylinders is not occurring when the absolute value |ΔX| of the difference ΔX is smaller than the threshold value ΔXth.

It should be noted that the third determining apparatus may obtain a ratio (Xs/Xz) of the final parameter Xs to the tentative parameter Xz in place of the absolute value |ΔX| of the difference ΔX, then determine that the air-fuel ratio imbalance (state) among cylinders is occurring when the ratio (Xs/Xz) is larger than the threshold value Rth, and determine that the air-fuel ratio imbalance (state) among cylinders is not occurring when the ratio (Xs/Xz) is smaller than the threshold value Rth.

It is preferable that the tentative parameter Xz be obtained while the air-fuel ratio of the exhaust gas varies (fluctuates) within "a range (a range A in FIG. 17) which is narrower than the stoichiometric air-fuel ratio region and includes the stoichiometric air-fuel ratio" so that the absolute value |ΔX| of the difference ΔX varies more greatly depending on whether or not "the air-fuel ratio imbalance (state) among cylinders is occurring".

Furthermore, the third determining apparatus may obtain a parameter obtaining period average air-fuel ratio which is an average air-fuel ratio while the parameter for imbalance determination is being obtained, and may perform the forced air-fuel-ratio-shift-control in a case in which the parameter for imbalance determination has been obtained while the parameter obtaining period average air-fuel ratio is within the stoichiometric air-fuel ratio region (or the region A), and the parameter for imbalance determination has not been obtained while the parameter obtaining period average air-fuel ratio is within the lean region or the rich region.

As described above, each of the determining apparatuses can determine whether or not the air-fuel ratio imbalance (state) among cylinders is occurring with high accuracy.

The present invention is not limited to the embodiments described above, various modifications may be adopted without departing from the scope of the invention. For example, the air-fuel-ratio-variation-indicative-value AFD obtained as the parameter for imbalance determination (the tentative parameter Xz and the final parameter Xs) may be one of the followings.

(P1) The air-fuel-ratio-variation-indicative-value AFD may be a value depending on (in accordance with) the trajectory length (basic indicative value) of the output value Vabyfs of the air-fuel ratio sensor 67 or the trajectory length (basic indicative value) of the detected air-fuel ratio abyfs. For example, the trajectory length of the detected air-fuel ratio abyfs may be obtained by obtaining the output value Vabyfs every time the constant sampling time period ts elapses, converting the output value Vabyfs into the detected air-fuel ratio abyfs, and integrating an absolute value of a difference between the detected air-fuel ratio abyfs and the detected air-fuel ratio obtained the sampling time period ts before.

It is preferable that the trajectory length be obtained for each of the unit combustion cycle period. An average value of the trajectory length for a plurality of unit combustion cycle periods (i.e., a value in accordance with the trajectory length) may be adopted as the air-fuel-ratio-variation-indicative-value AFD. It should be noted it is preferable that the threshold value Xth for imbalance determination be increased as the engine rotational speed NE increases if the parameter for imbalance determination based on the trajectory length of the output value Vabyfs or the trajectory length of the detected air-fuel ratio abyfs is used for the imbalance determination, since the they tend to increase as the engine rotational speed NE increases.

(P2) The air-fuel-ratio-variation-indicative-value AFD may be obtained as a value in accordance with a basic indicative value which is a change rate of (in) a change rate (i.e., a second order differential value with respect to time) of "the output value of the air-fuel ratio sensor 67 or the detected air-fuel ratio abyfs". For example, the air-fuel-ratio-variation-indicative-value AFD may be a maximum value of an absolute value of "the second order differential value $d^2(Vabyfs)/dt^2$ of the output value Vabyfs of the air-fuel ratio sensor 67" with respect to time for the unit combustion cycle period, or be a maximum value of an absolute value of "the second order differential value $d^2(abyfs)/dt^2$ of the detected air-fuel ratio represented by the output value Vabyfs of the air-fuel ratio sensor 67" with respect to time for the unit combustion cycle period.

For example, the change rate of the change rate of the detected air-fuel ratio abyfs can be obtained as follows.

The output value Vabyfs is obtained every time the constant sampling time period is elapses.

The output value Vabyfs is converted into the detected air-fuel ratio abyfs.

A difference between the detected air-fuel ratio abyfs and the previously detected air-fuel ratio abyfs obtained the constant sampling time period before is obtained as a change rate of the detected air-fuel ratio abyfs.

A difference between the change rate of the detected air-fuel ratio abyfs and the previous change rate of the detected air-fuel ratio abyfs obtained the constant sampling time period before is obtained as the change rate (the second order differential value $d^2(abyfs)/dt^2$) of the change rate of the detected air-fuel ratio abyfs.

In this case, among "a plurality of values of the change rate of the change rate of the detected air-fuel ratio abyfs, obtained in the unit combustion cycle period", "the value whose absolute value is the largest" is selected as a representative value. The representative values are obtained for a plurality of the unit combustion cycle periods, and an average value of absolute values of the plurality of the thus obtained representative values can be adopted as the air-fuel-ratio-variation-indicative-value AFD.

Further, each of the above determining apparatuses adopts the differential value d(abyfs)/dt (i.e., the detected air-fuel ratio changing rate ΔAF) as the basic indicative value, and adopts the value based on the average of the basic indicative values for the unit combustion cycle period as the air-fuel-ratio-variation-indicative-value AFD.

To the contrary, each of the determining apparatuses obtains the differential value d(abyfs)/dt (i.e., the detected air-fuel ratio changing rate ΔAF) as the basic indicative value, selects a value P1 whose absolute value is the largest among data of the differential value d(abyfs)/dt having a positive value for the unit combustion cycle period, selects a value P2 whose absolute value is the largest among data of the differential value d(abyfs)/dt having a negative value for the same unit combustion cycle period, and adopts, as the basic indicative value, the absolute value of the value P1 or the absolute value of the value P2, whichever is larger. Then, the determining apparatus may adopt, as air-fuel-ratio-variation-indicative-value AFD, an average value of the basic indicative values obtained for a plurality of the unit combustion cycle periods.

Furthermore, each of the determining apparatuses can be applied to a V-type engine, for example. In this case, the V-type engine may comprise, a right bank upstream side catalyst disposed at a position downstream of an exhaust-gas-aggregated-portion of two or more cylinders belonging to a right bank (a catalyst disposed in the exhaust passage of the engine and at a position downstream of the exhaust-gas-aggregated-portion into which the exhaust gases merge, the exhaust gases discharged from chambers of at least two or more of the cylinders among a plurality of the cylinders), a left bank upstream side catalyst disposed at a position downstream of an exhaust-gas-aggregated-portion of two or more cylinders belonging to a left bank (a catalyst disposed in the exhaust passage of the engine and at a position downstream of the exhaust-gas-aggregated-portion into which the exhaust gases merge, the exhaust gases discharged from chambers of two or more of the cylinders among the rest of the said at least two or more of the cylinders).

Further, the V-type engine may comprise an upstream side air-fuel ratio sensor for the right bank and a downstream side air-fuel ratio sensor for the right bank disposed upstream and downstream of the right bank upstream side catalyst, respectively, and may comprise upstream side air-fuel ratio sensor for the left bank and a downstream side air-fuel ratio sensor for the left bank disposed upstream and downstream of the left bank upstream side catalyst, respectively. Each of the upstream side air-fuel ratio sensors, similarly to the upstream side air-fuel ratio sensor 67, is disposed between the exhaust-gas-aggregated-portion of each bank and the upstream side catalyst of each bank. In this case, a main feedback control for the right bank and a sub feedback for the right bank are performed, and a main feedback control for the left bank and a sub feedback for the left bank are independently performed.

In this case, the determining apparatus may obtain "an air-fuel-ratio-variation-indicative-value AFD (parameter X for imbalance determination)" for the right bank based on the output value of the upstream side air-fuel ratio sensor for the right bank, and may determine whether or not an air-fuel ratio imbalance among cylinders belonging to the right bank is occurring with using the obtained value.

Similarly, the determining apparatus may obtain "an air-fuel-ratio-variation-indicative-value AFD (parameter X for imbalance determination)" for the left bank based on the output value of the upstream side air-fuel ratio sensor for the left bank, and may determine whether or not an air-fuel ratio imbalance among cylinders belonging to the left bank is occurring with using the obtained value.

In addition, each of the determining apparatus may vary the threshold value Xth for imbalance determination (including, the high side threshold XHith, and the low side threshold XLoth) in such a manner it is increased as the intake air flow rate Ga becomes larger. This is because the responsivity of the air-fuel ratio sensor 67 becomes lower as the intake air flow rate Ga becomes smaller, due to an existence of the protective covers 67b and 67c.

Furthermore, it is preferable that the high side threshold XHith be larger than or equal to the threshold value Xth for imbalance determination, the low side threshold XLoth be smaller than the threshold value Xth for imbalance determination. It should be noted that the high side threshold XHith may be smaller than the threshold value Xth for imbalance determination, as long as the high side threshold XHith is such that it is possible to clearly determine that an air-fuel ratio imbalance (state) among cylinders is occurring, when the tentative parameter Xz is higher than the high side threshold value XHith. Similarly, the low side threshold XLoth may be a value such that it is possible to clearly determine that an air-fuel ratio imbalance (state) among cylinders is not occurring, when the tentative parameter Xz is lower than the low side threshold value XLoth.

The invention claimed is:

1. An air-fuel ratio imbalance among cylinders determining apparatus, applied to a multi-cylinder internal combustion engine having a plurality of cylinders comprising:

an air-fuel ratio sensor, disposed at an exhaust-gas-aggregated-portion of an exhaust gas passage to which exhaust gases discharged from at least two or more cylinders of said plurality of cylinders aggregate or at a position downstream of said exhaust-gas-aggregated-portion in said exhaust gas passage, having an air-fuel ratio detection section including a solid electrolyte layer, an exhaust-gas-side electrode layer formed on one of surfaces of said solid electrolyte layer, a diffusion resistance layer which said exhaust gases reach and which covers said exhaust-gas-side electrode layer, an atmosphere-side electrode layer formed on the other one of surfaces of said solid electrolyte layer so as to be exposed to an air in an atmosphere chamber, said air-fuel ratio sensor outputting an output value varying depending on an air-fuel ratio of said exhaust gases passing through a position at which said air-fuel ratio sensor is disposed, based on a limiting-current flowing through said solid electrolyte layer caused by applying a predetermined electrical voltage between said exhaust-gas-side electrode layer and said atmosphere-side electrode layer;

a plurality of fuel injectors, each of said injectors provided in accordance with each of at least said two or more cylinders and injecting a fuel whose amount is in accordance with an instructed fuel injection amount, said fuel being contained in a mixture supplied to each of combustion chambers of said at least two or more cylinders; and an electric controller operatively connected to said plurality of fuel injectors, said electric controller configured to:

(a) control said instructed fuel injection amount in such a manner that an air-fuel ratio of said mixture supplied to said combustion chambers of said at least two or more cylinders coincides with a target air-fuel ratio;

(b) obtain, using said output value of said air-fuel ratio sensor, a parameter for imbalance determination which becomes larger as a variation of said air-fuel ratio of an exhaust gas passing through said position at which said air-fuel ratio sensor is disposed becomes larger;

(c) determine that an air-fuel ratio imbalance state among cylinders is occurring when said obtained parameter for imbalance determination is larger than a predetermined threshold value for imbalance determination, and to determine that said air-fuel ratio imbalance state among cylinders is not occurring when said obtained parameter for imbalance determination is smaller than said predetermined threshold value for imbalance determination;

(d) set said target air-fuel ratio at a non-stoichiometric air-fuel ratio which is an air-fuel ratio other than a stoichiometric air-fuel ratio and obtain said parameter for imbalance determination in a period in which a predetermined condition for obtaining a parameter for imbalance determination is satisfied, and to set said target air-fuel ratio at said stoichiometric air-fuel ratio in a period in which said predetermined condition for obtaining a parameter for imbalance determination is not satisfied;

(e) maintain said target air-fuel ratio at said stoichiometric air-fuel ratio and obtains said parameter for imbalance determination as a tentative parameter based on the output value of the air-fuel ratio sensor before it sets said target air-fuel ratio at said non-stoichiometric air-fuel ratio in said period in which said predetermined condition for obtaining a parameter for imbalance determination is satisfied;

(f) determine that said air-fuel ratio imbalance state among cylinders is occurring when said obtained tentative parameter is larger than a predetermined high side threshold value, (g) determine that said air-fuel ratio imbalance state among cylinders is not occurring when said obtained tentative parameter is smaller than a low side threshold value which is smaller than said high side threshold value by a predetermined amount;

(h) defer a determination as to whether or not said air-fuel ratio imbalance state among cylinders is occurring when said obtained tentative parameter is smaller than said high side threshold value and larger than said low side threshold value;

(i) set said target air-fuel ratio at said non-stoichiometric air-fuel ratio and obtains said parameter for imbalance determination based on said output value of said air-fuel ratio sensor as a final parameter, in a period in which said predetermined condition for obtaining a parameter for imbalance determination is satisfied in a case in which said determination as to whether or not said air-fuel ratio imbalance state among cylinders is occurring is deferred;

(j) determine that said air-fuel ratio imbalance state among cylinders is occurring when said obtained final parameter is larger than said threshold value for imbalance determination, and determines that said air-fuel ratio imbalance state among cylinders is not occurring when said obtained final parameter is smaller than said threshold value for imbalance determination; and (k) control said plurality of fuel injectors in response to said determination of said air-fuel ratio imbalance state among cylinders.

2. The air-fuel ratio imbalance among cylinders determining apparatus according to claim 1, wherein, said air-fuel ratio detection section of said air-fuel ratio sensor includes a catalytic section which facilitates an oxidation-reduction reaction and has an oxygen storage function; and said air-fuel sensor is configured in such a manner that said exhaust gas passing through said exhaust gas passage reaches said diffusion resistance layer via said catalytic section.

3. The air-fuel ratio imbalance among cylinders determining apparatus according to claim 1, wherein, said air-fuel sensor further comprises a protective cover, which accommodates said air-fuel ratio detecting section in its inside so as to cover said air-fuel detecting section, said cover including inflow holes for said exhaust gas passing through said exhaust gas passage to flow into said inside of said cover and outflow holes for said exhaust gas flowed into said inside of said cover to flow out to said exhaust gas passage.

* * * * *